United States Patent
Cheng et al.

(10) Patent No.: US 6,297,274 B1
(45) Date of Patent: *Oct. 2, 2001

(54) NONPEPTIDE ENDOTHELIN ANTAGONISTS WITH INCREASED WATER SOLUBILITY

(75) Inventors: Xue-Min Cheng; Annette Marian Doherty, both of Ann Arbor; William Chester Patt, Chelsea; Joseph Thomas Repine, Ann Arbor, all of MI (US)

(73) Assignee: Warner-Lambert Company, Morris Plains, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/117,667
(22) PCT Filed: Mar. 12, 1997
(86) PCT No.: PCT/US97/03929
§ 371 Date: Aug. 4, 1998
§ 102(e) Date: Aug. 4, 1998
(87) PCT Pub. No.: WO97/37985
PCT Pub. Date: Oct. 16, 1997

Related U.S. Application Data

(60) Provisional application No. 60/015,242, filed on Apr. 10, 1996.

(51) Int. Cl.[7] .............. A61K 31/34; C07D 265/30; C07D 405/00; C07D 307/02
(52) U.S. Cl. ............. 514/473; 544/106; 544/114; 544/129; 544/359; 546/207; 546/214; 548/517; 549/295; 549/320; 549/321
(58) Field of Search .................... 544/106, 114, 544/129, 359; 546/207, 214; 548/517; 549/295, 320, 321; 514/473

(56) References Cited

FOREIGN PATENT DOCUMENTS

WO 95 05376 * 2/1995 (WO) ............... 549/321

* cited by examiner

Primary Examiner—Joseph K. Mckane
Assistant Examiner—Joseph Murray
(74) Attorney, Agent, or Firm—Elizabeth M. Anderson; David R. Kurlandsky

(57) ABSTRACT

Novel nonpeptide endothelin I antagonists of Formula

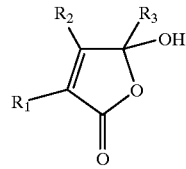

I are described wherein $R_1$ is unsubstituted or substituted cycloalkyl, phenyl, naphthyl or heteroaryl, $R_2$ is unsubstituted or substituted alkyl, aryl or heteroaryl, $R_3$ is unsubstituted or substituted alkyl, cycloalkyl, aryl or heteroayl, and $R_1$ and/or $R_2$ and/or $R_3$ are independently substituted by a total of from 1 to 4 substituents which enhance aqueous solubility with the proviso that when $R_2$ is alkyl and is substituted, the substituent is not oxygen at the α-position of the furanone ring. Further described are methods for the preparation and pharmaceutical compositions of compounds of Formula I, which are useful in treating atherosclerosis, restenosis, Raynaud's phenomenon, mild or severe congestive heart failure, cerebral ischemia, cerebral infarction, embolic stroke, cerebral vasospasm, glaucoma, subarachnoid hemorrhage, hemorrhagic stroke, diabetes, gastric ulceration and mucosal damage, ischemic bowel disease, Chrohn's disease, male penile erectile dysfunction, essential or malignant hypertension, pulmonary hypertension, pulmonary hypertension after bypass, cancer, especially malignant hemangioendothelioma or prostate cancer, myocardial infarction or ischemia, acute or chronic renal failure, renal ischemia, radiocontrast-induced nephrotoxcity, endotoxic, septic hemorrhagic shock, angina, preeclampsia, asthma, arrhythmias, benign prostatic hyperplasia, and elevated levels of endothelin.

29 Claims, No Drawings

NONPEPTIDE ENDOTHELIN ANTAGONISTS WITH INCREASED WATER SOLUBILITY

This application claim a right of provisional application Ser. No. 06/015,242 filed on Apr. 10, 1996.

BACKGROUND OF THE INVENTION

The present invention relates to novel antagonists of endothelin useful as pharmaceutical agents, to methods for their production, to pharmaceutical compositions which include these compounds and a pharmaceutically acceptable carrier, and to pharmaceutical methods of treatment. More particularly, the compounds of the present invention are antagonists of endothelin useful in treating elevated levels of endothelin, angina, arrhythmias, asthma, atherosclerosis, benign prostatic hyperplasia, Buerger's Disease, cardiac arrest, cardiogenic shock, cerebral trauma, Chrohn's Disease, chronic obstructive pulmonary disease, cryptogenic fibrosing alveolitis, congenital heart disease, congestive heart failure (CHF) (mild), congestive heart failure (CHF) (severe), cerebral ischemia, cerebral infarction, cerebral vasospasm, cirrhosis, diabetes, dilated cardiomyopathy, drowning (anoxia), endotoxic shock, gastric mucosal damage, glaucoma, head injury, hemodialysis, hemorrhagic shock, hypertension (essential), hypertension (malignant), hypertension (pulmonary), hypertension (pulmonary, after bypass), hypoglycemia, inflammatory arthritides, ischemic bowel disease, ischemic disease, male penis erectile dysfunction, malignant hemangioendothelioma, myocardial infarction, myocardial ischemia, prenatal asphyxia, postoperative cardiac surgery, prostate cancer, preeclampsia, Raynaud's Phenomenon, renal failure (acute), renal failure (chronic), renal ischemia, restenosis, sepsis syndrome, subarachnoid hemorrhage (acute), surgical operations, status epilepticus, stroke (thromboembolic), stroke (hemorrhagic), Takayasu's arteritis, ulcerative colitis, uremia after hemodialysis, and uremia before hemodialysis.

Endothelin-1 (ET-1), a potent vasoconstrictor, is a 21 amino acid bicyclic peptide that was first isolated from cultured porcine aortic endothelial cells. Endothelin-1, is one of a family of structurally similar bicyclic peptides which include: ET-2, ET-3, vasoactive intestinal contractor (VIC), and the sarafotoxins (SRTXs).

The distribution of the two cloned receptor subtypes, termed $ET_A$ and $ET_B$, have been studied extensively (Arai H., et al., Nature, 1990;348:730, Sakurai T., et al., Nature, 1990;348:732). The $ET_A$, or vascular smooth muscle receptor, is widely distributed in cardiovascular tissues and in certain regions of the brain (Lin H. Y., et al., Proc. Natl. Acad. Sci., 1991;88:3185). The $ET_B$ receptor, originally cloned from rat lung, has been found in rat cerebellum and in endothelial cells. The human ET receptor subtypes have been cloned and expressed (Sakamoto A., et al., Biochem. Biophys. Res. Chem., 1991;178:656, Hosoda K., et al., FEBS Lett., 1991;287:23). The $ET_A$ receptor clearly mediates vasoconstriction and there have been a few reports implicating the $ET_B$ receptor in the initial vasodilatory response to ET (Takayanagi R., et al., FEBS Lett., 1991;282:103). However, recent data has shown that the $ET_B$ receptor can also mediate vasoconstriction in some tissue beds (Panek R. L., et al., Biochem. Biophys. Res. Commun., 1992;183(2):566).

The involvement of endothelin has been proven in many human disease states.

Elevated levels of endothelin have been measured in patients suffering from ischemic heart disease (Yasuda M., et al., Amer. Heart J., 1990;119:801–806) and either stable or unstable angina (Stewart J. T., et al., Br. Heart J., 1991;66:7–9).

The degree of elevation of plasma ET levels in patients with heart failure varies from 2-fold to 5-fold (Stewart, et al., Circulation, 1992;85:510–517; Lerman, et al., J. Am. Coll. Cardiology, 1992;20:849–853). The greatest elevation measured appears to be in congestive heart failure (CHF) patients with marked pulmonary hypertension. The increased level of circulating ET in human congestive heart failure patients also correlated with the severity of the disease observed (Rodeheffer, et al., Am. J. Hypertension, 1991:4:9A; Rodeheffer, et al., Mayo Clin. Prod., 1992;67:719–724).

Many studies have indicated increased plasma levels of ET-1 after acute myocardial infarction (MI) in both animals and humans (Stewart, et al., J. Am. Coll. Cardiol., 1991:18:38–43; Tomoda, et al., Am. Heart J., 1993;125:667–672; Ray, et al., Br. Heart J., 1992;67:383–386; Tsuji, et al., Life Sci., 1991;48:1745–1749). It has also been reported that the action of ET-1 may be enhanced under the conditions of ischemia (Liu, et al., Biochem. Biophys. Res. Conmmun., 1989;164:1220–1225).

Several in vivo studies with ET antibodies have been reported in disease models. Left coronary artery ligation and reperfusion to induce myocardial infarction in the rat heart, caused a 4- to 7-fold increase in endogenous endothelin levels. Administration of ET antibody was reported to reduce the size of the infarction in a dose-dependent manner (Watanabe T., et al., "Endothelin in Myocardial Infarction," Nature, (Lond.) 1990;344:114). Thus, ET may be involved in the pathogenesis of congestive heart failure and myocardial ischemia (Margulies K. B., et al., "Increased Endothelin in Experimental Heart Failure," Circulation, 1990;82:2226).

Patients with chronic heart failure were treated with the ET antagonist Bosentan, which was found to improve cardiac performance, concluding that ET is involved in the regulation of vascular tone and that inhibition of its effects may be beneficial in chronic heart failure (Kiowski W., et al., Lancet, 1995;346:732–36, also J. Am. Coll. Cardiol., 1995; special edition 296A:779–1).

Infusion of an endothelin antibody 1 hour prior to and 1 hour after a 60 minute period of renal ischaemia resulted in changes in renal function versus control. In addition, an increase in glomerular platelet-activating factor was attributed to endothelin (Lopez-Farre A., et al., J. Physiology, 1991;444: 513–522). In patients with chronic renal failure as well as in patients on regular hemodialysis treatment mean plasma endothelin levels were significantly increased (Stockenhuber F., et al., Clin. Sci. (Lond.), 1992;82:255–258).

Studies by Kon and colleagues using anti-ET antibodies in an ischemic kidney model, to deactivate endogenous ET, indicated the peptide's involvement in acute renal ischemic injury (Kon V., et al., "Glomerular Actions of Endothelin In Vivo," J. Clin. Invest., 1989;83:1762).

Other investigators have reported that infusion of ET-specific antibodies into spontaneously hypertensive rats (SHR) decreased mean arterial pressure (MAP), and increased glomerular filtration rate and renal blood flow. In the control study with normotensive Wistar-Kyoto rats (WKY) there were no significant changes in these parameters (Ohno A., Effects of Endothelin-Specific Antibodies and Endothelin in Spontaneously Hypertensive Rats," J. Tokyo Women's Med. Coll., 1991;61:951).

Other studies have demonstrated the usefulness of ET antagonists in maintaining beneficial parameters of renal performance following ischemia-induced injuries (Mino, et al., *Eur. J. Pharmacol.*, 1992;221:77–83; Benigni, et al., *Kidney Int*, 1993;44:440–444).

$ET_A$ receptor mRNA has been detected in 82% of human meningiomas (*J. Clin. Invest.*, 1995;66:2017–2025

Plasma endothelin-1 levels were dramatically increased in a cancer patient with malignant hemangioendothelioma (Nakagawa K., et al., *Nippon Hifuka Gakkai Zasshi*, 1990;100:1453–1456).

Exogenous endothelin-1 is also a prostate cancer mitrogen in vitro. Endothelin levels are significantly elevated in men with metastatic prostate cancer. Every human prostate cancer cell line tested by Nelson et al., (*Nature Medicine*, 1995; Vol 1(9):944) produced ET-1 mRNA and secreted immunoreactive endothelin.

An ET antagonist, PD 155080 was found to mediate prostate smooth muscle function in vivo, which demonstrated that endothelin antagonists may be useful in the treatment of benign prostatic hyperplasia (Chleko I., et al., Annual Meeting of the American Urological Assn, Orlando, 1996).

The ET receptor antagonist BQ-123 has been shown to block ET-1 induced bronchoconstriction and tracheal smooth muscle contraction in allergic sheep providing evidence for expected efficacy in bronchopulmonary diseases such as asthma (Noguchi, et al., *Am. Rev. Respir. Dis.*, 1992;145(4 Part 2):A858).

Circulating endothelin levels are elevated in women with preeclampsia and correlate closely with serum uric acid levels and measures of renal dysfunction. These observations indicate a role for ET in renal constriction in preeclampsia (Clark B. A., et al., *Am. J. Obstet. Gynecol.*, 1992;166:962–968).

Plasma immunoreactive endothelin-1 concentrations are elevated in patients with sepsis and correlate with the degree of illness and depression of cardiac output (Pittett J., et al., *Ann. Surg.*, 1991;213(3):262).

In addition, the ET-1 antagonist BQ-123 has been evaluated in a mouse model of endotoxic shock. This $ET_A$ antagonist significantly increased the survival rate in this model (Toshiaki M., et al., 20.12.90. EP 0 436 189 A1).

Endothelin is a potent agonist in the liver eliciting both sustained vasoconstriction of the hepatic vasculature and a significant increase in hepatic glucose output (Gandhi C. B., et al., *Jornal of Biological Chemistry*, 1990;265(29):17432). In addition increased levels of plasma ET-1 have been observed in microalbuminuric insulin-dependent diabetes mellitus patients indicating a role for ET in endocrine disorders such as diabetes (Collier A., et al., *Diabetes Care*, 1992;15(8):1038).

Infusion of ET-1 produced a sustained, reversible, and salt-dependent hypertension when infused into normal, conscious rats (Mortensen, et al., *Hypertensrion*, 1990;15:720–723; Mortensen, et al., *FASEB J.*, 1991;5: A1105).

$ET_A$ antagonist receptor blockade has been found to produce an antihypertensive effect in normal to low renin models of hypertension with a time course similar to the inhibition of ET-1 pressor responses (Basil M. K., et al., *J. Hypertension*, 1992;10(Suppl. 4):S49). The endothelins have been shown to be arrhythmogenic, and to have positive chronotropic and inotropic effects, thus ET receptor blockade would be expected to be useful in arrhythmia and other cardiovascular disorders (Han S.-P., et al., *Life Sci.*, 1990;46:767).

Recently, an $ET_A$ selective antagonist demonstrated an oral antihypertensive effect (Stein P. D., et al., "The Discovery of Sulfonamide Endothelin Antagonists and the Development of the Orally Active $ET_A$ Antagonist 5-(Dimethylamino)-N-(3,4-dimethyl-5-isoxazolyl)-1-naphthalenesulfonamide," *J. Med. Chem.*, 1994;37: 329–331).

Plasma ET levels are elevated in patients with pulmonary hypertension (Yoshibayashi M., et al., *Circulation*, 1991;84:2280–2285). Increased expression has been measured indicating local production in the lung. Pulmonary hypertension is associated with the increased expression of endothelin-1 in vascular endothelial cells, suggesting that the local production of endothelin-1 may contribute to vascular abnormalities associated with pulmonary hypertension (Giaid A., et al., *N. Engl. J. Med.*, 1993;328:1732–9). In pulmonary hypertension, ET-1 is the most potent constrictor of airway smooth muscle thus far described in vitro (Pons, et al., *J. Pharmacol.*, 1991;102: 791–796). This response has been blocked by $ET_A$-receptor antagonists (Abraham, et al., *J. Appl. Physiol.*, 1993;74(5);2537–2542). Endothelin antagonists that block the production of endothelin and hence lower levels of endothelin have shown efficacy in several animal models of pulmonary hypertension. Pulmonary hypoxia increases ET-1 expression in the lung (*J. Surg. Res.*, 1994;57:280–283). For example, BQ-123, Bosentan, and PD 156707 provide protection in a rat hypoxia model of hypertension by lowering the increase in pulmonary vascular resistance and pulmonary arterial pressure (Eddahibi S., et al., *Am. J. Physiol.*, 1995;268: H828–835; Bonvallet S. T., et al., *Am. Rev. Resp.Dis.*, 1993;147: A493; IBC International Conference, R. Bialecki, Feb. 5, 1996, Coronado, Calif.). $ET_A$-receptor antagonists have been found to prevent and reverse chronic hypoxia-induced pulmonary hypertension in rat (DiCarlo, et al., *Am. J. Physiol.*, 1995;269: L690-L697; Chen, et al., *J. Appl. Physiol.*, 1995;79(6):2122–2131).

There is evidence that suggests the extent of increase in plasma ET-1 levels in patients with pulmonary hypertension may reflect the abnormalities of pulmonary circulation. It has been demonstrated that the pulmonary artery endothelial cells are injured in patients with congenital heart disease (Ishikawa S., et al., *J. Thorac. Cardiovasc. Surg.*, 1995;110:271–3) Further, in cardiopulmonary bypass operations on patients with congenital heart disease, an immediate postoperative increase in circulating endothelin was observed which may predispose the patient to pulmonary vascular lability and crises in the postoperative period (Komai H., et al., *J. Thora. Cardiovasc. Surg.*, 1993;106:473–8).

The widespread localization of the endothelins and their receptors in the central nervous system and cerebrovascular circulation has been described (Nikolov R. K., et al., *Drugs of Today*, 1992;28(5): 303–310). Intracerebroventricular administration of ET-1 in rats has been shown to evoke several behavioral effects. The potent vasoconstrictor action of ETs on isolated cerebral arterioles suggests the importance of these peptides in the regulation of cerebrovascular tone. These factors strongly suggest a role for the ETs in neurological disorders.

The volume of ischemic damage in the cerebral hemisphere of cats following middle cerebral artery occlusion was significantly reduced after the IV administration of PD 156707 (Patel, et al., *J. Cardiovasc. Pharmacol.*, 1995;26 (Suppl. 3):S412–S415). Reduction of ischemic brain injury in rats was also demonstrated following oral administration of the endothelin antagonist SB 217242 (Barone, et al., *J. Cardiovasc. Pharmacol.*, 1995;26(Suppl. 3): S404–S407).

Several studies have shown that endothelin levels are elevated in acute and chronic renal failure (Torralbo A., et al., *Am. J. Kid. Dis.*, 1995;25(16):918–923). Data in models of acute renal failure indicate that endothelin plays an important role. An endothelin receptor antagonist Bosentan that can block endothelin production and thereby lower levels has been reported to be effective in models of acute renal ischemia (Clozel M., et al., *Nature*, 1995;365:759). In dogs, the endothelin receptor antagonist SB 2090670 can attenuate ischemia-induced reductions in glomerular filtration rate and increases in fractional sodium excretion (Brooks D. P., et al., *J. Pharmacol. Exp. Ther.*, 1995). In addition, several antagonists have been shown to block radiocontrast-induced nephrotoxicity (Oldroyd S., et al., *Radiology*, 1995;196:661–665).

TAK-044 has shown protective effects in a model of acute renal failure in rats (*Life Sci.*, 1994;55(4):301–310).

The $ET_A$ antagonist BQ-123 has been shown to prevent early cerebral vasospasm following subarachnoid hemorrhage (SAH) (Clozel M. and Watanabe H., *Life Sci.*, 1993;52:825–834; Lee K. S., et al., *Cerebral Vasospasm*, 1993:217; and *Neurosugery*, 1994;34:108). FR 139317 significantly inhibited the vasoconstriction of the basilar artery after 7 days in a canine two-hemorrhage model of SAH (Nirei H., et al., *Life Sci.*, 1993;52:1869). BQ-485 also significantly inhibited the vasoconstriction of the basilar artery after 7 days in a canine two-hemorrhage model of SAH (Yano, et al., *Biochem. Biophys. Res. Commun.*, 1993; 195:969). Ro 46-2005 (Clozel M., et al., *Nature*, 1993;365:759) has been shown to prevent early cerebral vasospasm following SAH in the rat with no significant effect on systemic arterial blood pressure. Treatment with Ro 47-0203=Bosentan (Clozel, et al., *Circulation*, 1993;88(4) part 2:0907) to rabbits with SAH had a 36±7% reduction of basilar artery cross-sectional area compared to sham rabbits. All of these studies show in vivo efficacy of endothelin antagonists in cerebral vasospasm resulting from SAH.

Circulating and tissue endothelin immunoreactivity is increased more than 2-fold in patients with advanced atherosclerosis (Lerman A., et al., *New England J.T Med.*, 1991;325:997–1001). Increased endothelin immunoreactivity has also been associated with Buerger's disease (Kanno K., et al., *J. Amer. Med. Assoc.*, 1990;264:2868) and Raynaud's phenomenon (Zamora M. R., et al., *Lancet*, 1990;336:1144–1147).

An increase of circulating endothelin levels was observed in patients that underwent percutaneous transluminal coronary angioplasty (PTCA) (Tahara A., et al., *Metab. Clin. Exp.*, 1991;40:1235–1237).

In an experiment to minimize restenosis following carotid artery balloon angioplasty in rats, the ET receptor antagonist SB 209670 was found to ameliorate neointima formation (Douglas, et al., *Circulation Res.*, 1994;75:190–197).

Local intra-arterial administration of endothelin has been shown to induce small intestinal mucosal damage in rats in a dose-dependent manner (Mirua S., et al., *Digestion*, 1991;48:163–172; Masuda E., et al., *Am. J. Physiol.*, 1992;262: G785–G790). Elevated endothelin levels have been observed in patients suffering from Crohn's disease and ulcerative colitis (Murch S. H., et al., *Lancet*, 1992;339:381–384).

The ET receptor antagonist bosentan was found to be an antagonist toward the ET-1-induced changes in gastric mucosal hemodynamics as well as on ET-1-induced gastric ulceration (Lazaratos, et al., *Pharmacol. Lett.*, 1995;56(9):195–200).

Graefe's *Arch. Clin. Exp. Ophthalmol*, 1995;233(8):484–488 provides data to support the hypothesis that vascular dysfunction may be involved in the pathogenesis of optic nerve damage in normal-tension glaucoma.

*Eur. J. Pharmacol.*, 1996;307(1):69–74 teaches a role for endothelins in penile erection.

Release of eicosanoids and endothelin in an experimental model of adult respiratory distress syndrome (ARDS) is covered in *Agents Actions Suppl., Prostaglandins Cardiovasc. Syst.*, 1992;37:41–6.

*Am. Rev. Respir. Dis.*, 1993;148:1169–1173 teaches venous ET-1 concentrations are massively increased in ARDS as a result of both increased formation and decreased clearance.

*Chest*, 1993;104:476–80 shows plasma ET-1 levels also positively correlate with right atrial pressure, systolic pulmonary arterial pressure, mean pulmonary arterial pressure, and resistance ratio (pulmonary vascular resistance/systemic vascular resistance) in ARDS.

In chronic obstructive pulmonary disease (COPD) and Cor Pulmonale associated with pulmonary hypertension patients excrete higher amounts of ET-1 compared to healthy subjects. Urinary ET-1 levels are further increased during acute exacerbation of the disease.

ET-1 levels in broncho alveolar lavage fluid from patients with COPD have been reported. ET-1 is involved in pulmonary endothelium damage caused by hypoxia in COPD patients. Pulmonary artery hypertension is the primary cardiovascular complication in COPD. (See Sofia, et al., *Respiration*, 1994:263–268(61); "Increased 24-Hour endothelin-1 urinary excretion in patients with chronic obstructive pulmonary disease" and Matthay, et al., *Medical Clinics of North America*, 1990:571–618(74); "Cardiovascular pulmonary interaction in chronic obstructive pulmonary disease with special reference to the pathogenesis and management of Cor Pulmonale."

ET-1 expression is increased in the lung vasculature of patients with pulmonary hypertension contributes to the medial hyperplasia and atrial fibrosis of cryptogenic fibrosing alveolitis. See Giaid, et al., *The Lancet*, 1993:1550–1554 (341) Expression of endothelin-1 in lungs of patients with cryptogenic fibrosing alveolitis.

In summary, some of the conditions in which ET antagonists may be useful in treatment are as follows: angina, arrhythmias, asthma, atherosclerosis, benign prostatic hyperplasia, Buerger's Disease, cardiac arrest, cardiogenic shock, cerebral trauma, Chrohn's Disease, chronic obstructive pulmonary disease, cryptogenic fibrosing alveolitis, congenital heart disease, congestive heart failure (CHF) (mild), congestive heart failure (CHF) (severe), cerebral ischemia, cerebral infarction, cerebral vasospasm, cirrhosis, diabetes, dilated cardiomyopathy, drowning (anoxia), endotoxic shock, gastric mucosal damage, glaucoma, head injury, hemodialysis, hemorrhagic shock, hypertension (essential), hypertension (malignant), hypertension (pulmonary), hypertension (pulmonary, after bypass), hypoglycemia, inflammatory arthritides, ischemic bowel disease, ischemic disease, male penile erectile dysfunction, malignant hemangioendothelioma, myocardial infarction, myocardial ischemia, prenatal asphyxia, postoperative cardiac surgery, prostate cancer, preeclampsia, Raynaud's Phenomenon, renal failure (acute), renal failure (chronic), renal ischemia, restenosis, sepsis syndrome, subarachnoid hemorrhage (acute), surgical operations, status epilepticus, stroke (thromboembolic), stroke (hemorrhagic), Takayasu's arteritis, ulcerative colitis, uremia after hemodialysis, and uremia before hemodialysis.

TABLE I

Plasma Concentrations of ET-1 in Humans

| Condition | Normal Control | ET Plasma Levels Reported (pg/mL) |
|---|---|---|
| Atherosclerosis | 1.4 | 3.2 pmol/L |
| Surgical operation | 1.5 | 7.3 |
| Buerger's disease | 1.6 | 4.8 |
| Takayasu's arteritis | 1.6 | 5.3 |
| Cardiogenic shock | 0.3 | 3.7 |
| Congestive heart failure (CHF) | 9.7 | 20.4 |
| Mild CHF | 7.1 | 11.1 |
| Severe CHF | 7.1 | 13.8 |
| Dilated cardiomyopathy | 1.6 | 7.1 |
| Preeclampsia | 10.4 pmol/L | 22.6 pmol/L |
| Pulmonary hypertension | 1.45 | 3.5 |
| Acute myocardial infarction | 1.5 | 3.3 |
| (several reports) | 6.0 | 11.0 |
| | 0.76 | 4.95 |
| | 0.50 | 3.8 |
| Subarachnoid hemorrhage | 0.4 | 2.2 |
| Crohn's Disease | 0–24 fmol/mg | 4–64 fmol/mg |
| Ulcerative colitis | 0–24 fmol/mg | 20–50 fmol/mg |
| Cold pressor test | 1.2 | 8.4 |
| Raynaud's phenomenon | 1.7 | 5.3 |
| Raynaud's/hand cooling | 2.8 | 5.0 |
| Hemodialysis | <7 | 10.9 |
| (several reports) | 1.88 | 4.59 |
| Chronic renal failure | 1.88 | 10.1 |
| Acute renal failure | 1.5 | 10.4 |
| Uremia before hemodialysis | 0.96 | 1.49 |
| Uremia after hemodialysis | 0.96 | 2.19 |
| Essential hypertension | 18.5 | 33.9 |
| Sepsis syndrome | 6.1 | 19.9 |
| Postoperative cardiac | 6.1 | 11.9 |
| Inflammatory arthritides | 1.5 | 4.2 |
| Malignant hemangioendothelioma | 4.3 (after removal) | 16.2 |

Allen C. F. H., Frame G. F., *Can. J. Research*, 1932; 6:605 teaches the condensation of methyl and ethyl α-phenyl-β-(para-substituted)benzoylpropionates with benzaldehyde and piperonal in the presence of sodium methylate, followed by acidification, produces cyclic compounds.

Allen C. F. H., Frame G. F., Normington J. B., Wilson C. V., *Can. J. Research*, 1933;8:137 teaches the condensation of benzaldehyde with methyl and ethyl α-aryl-β-benzoylpropionates in the presence of sodium methylate, followed by acidification, to give unsaturated ketonic acids.

Allen, C. F., Normington, J. B., Wilson, C. V., *Can. Research*, 1934; 11:382 recites a number of highly substituted acrylic acids or their lactols.

Allen, C. F. H., Davis, T. J., Stewart, D. W., VanAllan, J. A., *Can. J. Chem.*, 1956;34:926 shows that α aryl-β-aroylpropionic acids exist in an open-chain configuration while the condensation products of these latter acids with aromatic aldehydes are lactols, refuting his previous article *Can. J. Research*, 1933;8:137.

Copending U.S. Pat. No. 5,691,373 covers nonpeptide endothelin antagonists of Formula II

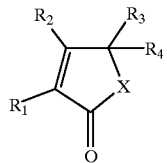

II or a tautomeric open chain ketoacid form thereof or a pharmaceutically acceptable salt thereof wherein $R_1$ is cycloalkyl substituted or unsubstituted of from 3 to 12 carbon atoms,
phenyl substituted with from 1 to 5 substituents,
naphthyl unsubstituted or substituted with from 1 to 5 substituents, or
heteroaryl unsubstituted or substituted with from 1 to 5 substituents;

$R_2$ is alkyl substituted or unsubstituted straight, or branched of from 1 to 12 carbon atoms,
cycloalkyl substituted or unsubstituted of from 3 to 12 carbon atoms,
aryl which is unsubstituted or substituted with from 1 to 5 substituents,
heteroaryl which is unsubstituted or substituted with from 1 to 3 substituents;

$R_3$ is alkyl substituted or unsubstituted straight, or branched, of from 1 to 12 carbon atoms,
cycloalkyl substituted or unsubstituted of from 3 to 12 carbon atoms,
aryl which is unsubstituted or substituted with from 1 to 5 substituents,
heteroaryl which is unsubstituted or substituted with from 1 to 3 substituents;

$R_4$ is hydroxy or $OR_5$,
$SR_5$, wherein $R_5$ is alkyl or substituted alkyl of from 1 to 7 carbon atoms, or
$(CH_2)_n OR_5$ wherein n is an integer of from 1 to 3;

X is O or S;

with the proviso that when $R_1$ is monosubstituted phenyl and the substituent is p-methoxy, $R_3$ is not unsubstituted phenyl, monosubstituted phenyl, or mesityl and with the further proviso when $R_2$ is alkyl substituted, the substituent is not oxygen at the α-position to the furanone ring.

This patent is hereby incorporated by reference.

Compounds of Formula

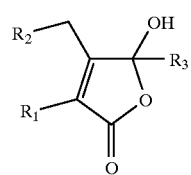

IA wherein:

| $R_1$ | $R_2$ | $R_3$ |
|---|---|---|
| phenyl | phenyl | phenyl |
| phenyl | phenyl | p-chloro-phenyl |

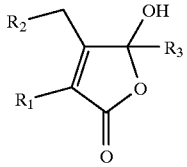

wherein:

| R₁ | R₂ | R₃ |
|---|---|---|
| phenyl | phenyl | p-bromo-phenyl |
| piperonyl | 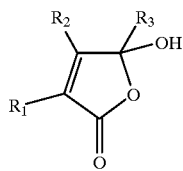 | phenyl | p-chloro-phenyl |
| phenyl | o-chlorophenyl | phenyl |
| phenyl | phenyl | p-phenyl-phenyl |
| anisyl (p-methoxyphenyl) | phenyl | phenyl |
| anisyl | α-furyl | phenyl |
| phenyl | piperonyl | p-chloro-phenyl |
| anisyl | o-chlorophenyl | phenyl |
| anisyl | o-methoxy-phenyl | phenyl |
| phenyl | phenyl | mesityl |
| phenyl | phenyl | p-methyl-phenyl |
| phenyl | o-chlorophenyl | p-chloro-phenyl |
| phenyl | phenyl | p-methoxy-phenyl |
| anisyl | o-methylphenyl | phenyl |
| phenyl | piperonyl | p-bromo-phenyl |
| phenyl | piperonyl | p-methoxy-phenyl | are all known. However, the methods of using 2(5H)-furanone, 3-(1,3-benzodioxol-5-yl)-5-(4-chlorophenyl)-5-hydroxy-4-(phenylmethyl)- and a pharmaceutical composition containing it are taught in the above co-pending application.

SUMMARY OF THE INVENTION

The instant invention is a compound of Formula I

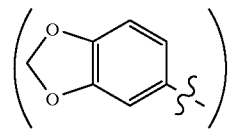

or a tautomeric open chain keto-acid form thereof or a pharmaceutically acceptable salt thereof wherein
  $R_1$ is cycloalkyl of from 3 to 12 carbon atoms substituted or unsubstituted,
    phenyl substituted with from 1 to 5 substituents,
    naphthyl unsubstituted or substituted with from 1 to 5 substituents, or
    heteroaryl unsubstituted or substituted with from 1 to 5 substituents;

$R_2$ is straight or branched alkyl of from 1 to 12 carbon atoms substituted or unsubstituted,
    cycloalkyl of from 3 to 12 carbon atoms substituted or unsubstituted,
    aryl unsubstituted or substituted with from 1 to 5 substituents, or
    heteroaryl unsubstituted or substituted with from 1 to 3 substituents;
  $R_3$ is straight or branched alkyl of from 1 to 12 carbon atoms substituted or unsubstituted,
    cycloalkyl of from 3 to 12 carbon atoms substituted or unsubstituted,
    aryl which is unsubstituted or substituted with from 1 to 5 substituents, or
    heteroaryl unsubstituted or substituted with from 1 to 3 substituents;
  at least one of $R_1$ or $R_2$ or $R_3$ is substituted by a substituent which enhances aqueous solubility. Up to four aqueous solubility groups may be attached independently to $R_1$ and/or $R_2$ and/or $R_3$. These aqueous solubility enhancing groups consist of secondary aminos, tertiary aminos (where the tertiary amino may be a cyclic structure and further may contain additional hetero atoms) or a sulfonic acid moiety; with the proviso that when $R_2$ is alkyl and is substituted, the substituent is not oxygen at the α-position to the furanone ring.

Preferred compounds of the instant invention are those of Formula I wherein
  $R_1$ is phenyl substituted with from 1 to 5 substituents,
  $R_2$ is straight or branched alkyl of from 1 to 9 carbon atoms substituted with from 1 to 7 substitutents,
  $R_3$ is aryl substituted or unsubstituted;
at least one of Groups $R_1$ or $R_2$ or $R_3$ is substituted by a substituent which enhances aqueous solubility. Up to four aqueous solubility groups may be attached independently to $R_1$ and/or $R_2$ and/or $R_3$. These aqueous solubility enhancing groups consist of secondary aminos, tertiary aminos (where the tertiary amino may be a cyclic structure and further may contain additional hetero atoms) or a sulfonic acid moiety; with the proviso when $R_2$ is alkyl and is substituted, the substituent is not oxygen at the α-position to the furanone ring. In those cases where $R_2$ is a substituted aryl or heteroaryl group, the aqueous solubilizing group would be attached to the aryl or heteroaryl.

More preferred compounds of the instant invention are those of Formula I wherein
  $R_1$ is phenyl substituted with from 1 to 5 substituents;
  $R_2$ is straight or branched alkyl of from 1 to 7 carbons substituted with from 1 to 7 substituents;
  $R_3$ is aryl substituted or unsubstituted;
  At least one of the substituents on $R_1$ and/or $R_2$ and/or $R_3$ have a substituent selected from:

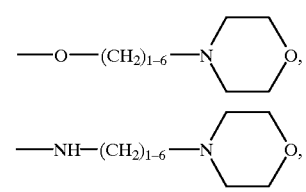

—O—$(CH_2)_{1-6}N(R_4)_2$,
—NH—$(CH_2)_{1-6}N(R_4)_2$ wherein $R_4$ is alkyl of from 1 to 6 carbons,

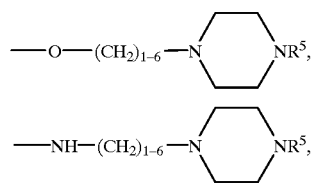

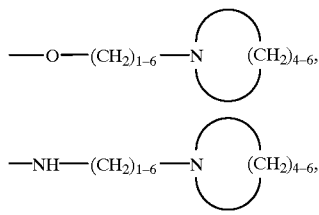

wherein $R^5$ is hydrogen or lower alkyl,

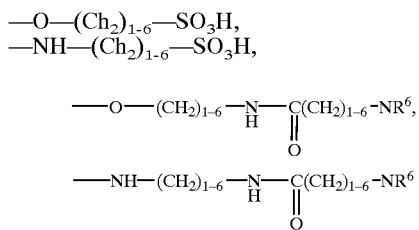

wherein $R^6$ is alkyl of from 1 to 6 carbons,

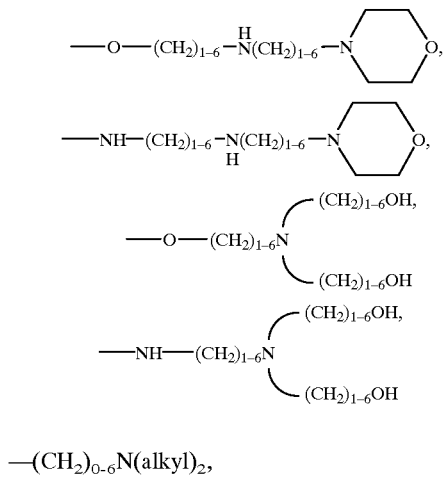

—$(CH_2)_{0-6}N(alkyl)_2$,

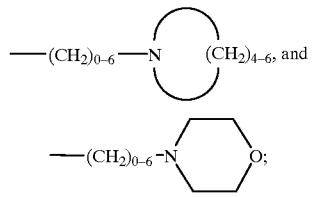

with the proviso that when $R_2$ is alkyl and is substituted, the substituent is not oxygen at the α-position to the furanone ring.

More preferred compounds of the instant invention are those of Formula I wherein $R_1$ is 4-piperonyl,
3,5-dimethoxyphenyl, or
3-methoxy-4,5-methylenedioxyphenyl;

$R_2$ is 4-(3-dimethylaminopropoxy)benzyl,
3-(3-dimethylaminopropoxy)benzyl,
5-(3-dimethylaminopropoxy)-3,4-dimethoxybenzyl,
5-(2-morpholin-4-yl-ethoxy)-3,4-dimethoxybenzyl,
5-(3-morpholin-4-yl-propoxy)-3,4-dimethoxybenzyl,
5-(3-(4-methyl-piperazin-1-yl)propoxy)-3,4-dimethoxybenzyl,
5-(2-(4-methyl-piperazin-1-yl)ethoxy)-3,4-dimethoxybenzyl,
4-(2-(4-methyl-piperazin-1-yl)ethoxy)benzyl,
3-(2-(4-methyl-piperazin-1-yl)ethoxy)benzyl,
4-(3-(4-methyl-piperazin-1-yl)propoxy)benzyl,
3-(3-(4-methyl-piperazin-1-yl)propoxy)benzyl,
4-(2-morpholin-4-yl-ethoxy)benzyl,
3-(2-morpholin-4-yl-ethoxy)benzyl,
4-(2-pyrrolidinyl-ethoxy)benzyl,
3-(2-pyrrolidinyl-ethoxy)benzyl,
4-(3-pyrrolidinyl-propoxy)benzyl,
3-(3-pyrrolidinyl-propoxy)benzyl,
5-(3-pyrrolidinyl-propoxy)-3,4-dimethoxybenzyl,
5-(2-pyrrolidinyl-ethoxy)-3,4-dimethoxybenzyl,
3,4,5-trimethoxybenzyl, benzyl;

$R_3$ is 3,4-dimethoxyphenyl,
3-methyl-4-methoxyphenyl,
2,4-dimethoxyphenyl,
4-methoxyphenyl,
4-(3-dimethylaminopropoxy)phenyl, or
4-(2-morpholin-4-ylethoxy)phenyl;

$R_4$ is hydroxy; and at least one $R_1$ and/or $R_2$ and/or $R_3$ is substituted by a substituent which enhances aqueous solubility and up to four aqueous solubility groups may be attached independently to $R_1$ and/or $R_2$ and/or $R_3$. These aqueous solubility enhancing groups consist of secondary aminos, tertiary aminos (where the tertiary amino may be a cyclic structure and further may contain additional hetero atoms) or a sulfonic acid moiety.

Still more preferred compounds of the instant invention are selected from:

3-Benzo[1,3]dioxol-5-yl-4-[4-(3-dimethylamino-propoxy)-benzyl]-5-hydroxy-5-(4-methoxy-phenyl)-5H-furan-2-one, 2-{5-[4-Benzo[1,3]dioxol-5-yl-2-hydroxy-2-(4-methoxy-phenyl)-5-oxo-2,5-dihydro-furan-3-ylmethyl]-2,3-dimethoxy-phenoxy}-N-(2-morpholin-4-yl-ethyl)-acetamide, 3-Benzo[1,3]dioxol-5-yl-5-hydroxy-5-[4-(2-morpholin-4-yl-ethoxy)-phenyl]-4-(3,4,5-trimethoxy-benzyl)-5H-furan-2-one, 3-Benzo[1,3]dioxol-5-yl-4-[3,4-dimethoxy-5-(2-morpholin-4-yl-ethoxy)-benzyl]-5-hydroxy-5-(4-methoxy-phenyl)-5H-furan-2-one, 3-Benzo[1,3]dioxol-5-yl-4-[3-(2-dimethylamino-ethoxy)-benzyl]-5-hydroxy-5-(4-methoxy-phenyl)-5H-furan-2-one, 3-Benzo[1,3]dioxol-5-yl-4-[3-(3-dimethylamino-propoxy)-benzyl]-5-hydroxy-5-(4-methoxy-phenyl)-5H-furan-2-one, 3-Benzo[1,3]dioxol-5-yl-5-hydroxy-5-(4-methoxy-phenyl)-4-[3-(2-morpholin-4-yl-ethoxy)-benzyl]-5H-furan-2-one, 3-Benzo[1,3]dioxol-5-yl-5-[4-(3-dimethylamino-propoxy)-phenyl]-5-hydroxy-4-(3,4,5-trimethoxy-benzyl)-5H-furan-2-one, 3-Benzo[1,3]dioxol-5-yl-4-[3-(3-dimethylamino-propoxy)-4,5-dimethoxy-benzyl]-5-hydroxy-5-(4-methoxy-phenyl)-5H-furan-2-one, 3-Benzo[1,3]dioxol-5-yl-5-hydroxy-4-[3-methoxy-4,5-bis-(2-morpholin-4-yl-ethoxy)-benzyl]-5-(4-methoxy-phenyl)-5H-furan-2-one, 4-(3-Dimethylaminomethyl-benzyl)-5-hydroxy-3-(7-methoxy-benzo[1,3]dioxol-5-yl)-5-(4-methoxy-phenyl)-5H-furan-2-one, 3-(3-Dimethylaminomethyl-benzyl)-2-(7-methoxy-benzo[1,3]dioxol-5-yl)-4-(4-methoxy-phenyl)-4-oxo-but-2-enoic acid monosodium salt, 3-Benzo[1,3]dioxol-5-yl-4-[3-(2-dimethylamino-ethoxy)-4,5-dimethoxy-benzyl]-5-hydroxy-5-(4-methoxy-phenyl)-5H-furan-2-one, 3-Benzo[1,3]dioxol-5-yl-4-[3,4-dimethoxy-5-(3-morpholin-4-yl-propoxy)-benzyl]-5-hydroxy-5-(4-methoxy-phenyl)-5H-furan-2-one, 3-Benzo[1,3]dioxol-5-yl-4-{3,4-dimethyoxy-5-[3-(4-methyl-piperazin-1-yl)-propoxy]-benzyl}-5-hydroxy-5-(4-methoxy-phenyl)-5H-furan-2-one, 3-Benzo[1,3]dioxol-5-yl-5-[2-(3-dimethylamino-propoxy)-4-methoxy-phenyl]-5-hydroxy-4-(3,4,5-trimethoxy-benzyl)-5H-furan-2-one, 3-{5-[4-Benzo[1,3]dioxol-5-yl-2-hydroxy-2-(4-methoxy-phenyl)-5-oxo-2,5-dihydro-furan-3-ylmethyl]-2,3-dimethoxy-phenoxy}-propane-1-sulfonic acid, 3-{5-[4-Benzo[1,3]dioxol-5-yl-2-hydroxy-2-(4-methoxy-phenyl)-5-oxo-2,5-dihydro-furan-3-ylmethyl]-2,3-dimethoxy-phenoxy}-butane-1-sulfonic acid, 3-{5-[4-Benzo[1,3]dioxol-5-yl-2-hydroxy-2-(4-methoxy-phenyl)-5-oxo-2,5-dihydro-furan-3-ylmethyl]-2,3-dimethoxy-phenoxy}-ethane-1-sulfonic acid, 3-{5-[4-Benzo[1,3]dioxol-5-yl-2-hydroxy-2-(4-methoxy-phenyl)-5-oxo-2,5-dihydro-furan-3-ylmethyl]-2,3-dimethoxy-phenoxy}-pentane-1-sulfonic acid, 3-Benzo[1,3]dioxol-5-yl-4-(3-dimethylaminomethyl-benzyl)-5-hydroxy-5-(4-methoxy-phenyl)-5H-furan-2-one, 3-Benzo[1,3]dioxol-5-yl-5-hydroxy-5-(4-methoxy-phenyl)-4-(3-methylamino-benzyl)-5H-furan-2-one, 3-Benzo[1,3]dioxol-5-yl-5-hydroxy-5-(4-methoxy-phenyl)-4-{3-[3-(4-methyl-piperazin-1-yl)-propoxy]-benzyl}-5H-furan-2-one, 3-Benzo[1,3]dioxol-5-yl-5-hydroxy-5-(4-methoxy-phenyl)-4-[3-(3-morpholin-4-yl-propoxy)-benzyl]-5H-furan-2-one, 3-[3-(2-Dimethylamino-ethoxy)-5-methoxy-phenyl]-5-hydroxy-5-(4-methoxy-phenyl)-4-(3,4,5-trimethoxy-benzyl)-5H-furan-2-one, 3-(3,5-Dimethoxy-phenyl)-4-[3-(2-dimethylamino-ethoxy)-4,5-dimethoxy-benzyl]-5-hydroxy-5-(4-methoxy-phenyl)-5H-furan-2-one, and 4-{3,4-Dimethoxy-5-[3-(4-methyl-piperazin-1-yl)-propoxy]-benzyl}-3-(3,5-dimethoxy-phenyl)-5-hydroxy-5-(4-methoxy-phenyl)-5H-furan-2-one.

Elevated levels of endothelin have been shown to be involved in a number of pathophysiological states including angina, arrhythmias, asthma, atherosclerosis, benign prostatic hyperplasia, Buerger's Disease, cardiac arrest, cardiogenic shock, cerebral trauma, Chrohn's Disease, congenital heart disease, congestive heart failure (CHF) (mild), congestive heart failure (CHF) (severe), cerebral ischemia, cerebral infarction, cerebral vasospasm, cirrhosis, diabetes, dilated cardiomyopathy, drowning (anoxia), endotoxic shock, gastric mucosal damage, head injury, hemodialysis, hemorrhagic shock, hypertension (essential), hypertension (malignant), hypertension (pulmonary), hypertension (pulmonary, after bypass), hypoglycemia, inflammatory arthritides, ischemic bowel disease, ischemic disease, malignant hemangioendothelioma, myocardial infarction, myocardial ischemia, prenatal asphyxia, postoperative cardiac surgery, prostate cancer, preeclampsia, Raynaud's Phenomenon, renal failure (acute), renal failure (chronic), renal ischemia, restenosis, sepsis syndrome, subarachnoid hemorrhage (acute), surgical operations, status epilepticus, stroke (thromboembolic), stroke (hemorrhagic), Takayasu's arteritis, ulcerative colitis, uremia after hemodialysis, and uremia before hemodialysis. As antagonists of endothelin, the compounds of Formula I are useful in their treatment.

A still further embodiment of the present invention is a pharmaceutical composition for administering a therapeutically effective amount of a compound of Formula I in unit dosage form in the treatment methods mentioned above.

Finally, the present invention is directed to methods for production of a compound of Formula I.

DETAILED DESCRIPTION OF THE INVENTION

The solubilizing groups are selected from secondary or tertiary amino groups and sulfonic acids. The secondary amino groups are substituted by straight or branched chain alkyl, aryl, and heteroaryl, each of which can be either unsubstituted or substituted by alkoxy, hydroxy, alkyl, carboxy, carboethoxy, carbomethoxy, amino, monosubstituted amino, disubstituted amino, and nitro. The tertiary amino group has substituents independently selected from straight or branched alkyl which is unsubstituted or substituted by alkoxy, hydroxy, alkyl, carboxy, carboethoxy, carbomethoxy, amino, monosubstituted amino, disubstituted amino, and nitro. Other substituents are aryl and heteroaryl groups, each of which can be substituted or unsubstituted.

The substituents on the tertiary amino group can form a ring with the nitrogen into which they are attached, and may optionally contain additional heteroatoms such as N—R, O or S, such groups as morpholinyl, piperazinyl, and pyrrolidinyl. Preferred are the morpholinyl, piperazinyl, and 4-methyl piperazinyl solubilizing groups.

In the compounds of Formula I, the term "alkyl" means a straight or branched hydrocarbon radical having from 1 to 12 carbon atoms unless otherwise specified and includes, for example, methyl, ethyl, n-propyl, isopropyl, n-butyl, sec-butyl, isobutyl, tert-butyl, allyl, n-pentyl, n-hexyl, n-heptyl, n-octyl, n-nonyl, n-decyl, undecyl, and dodecyl. The alkyl group is unsubstituted or substituted by from 1 to 3 substituents selected from alkyl, alkoxy, thioalkoxy all as defined herein, hydroxy, thiol, nitro, halogen, amino, mono and disubstituted amino, formyl, cycloalkyl, carboxyl, nitrile,

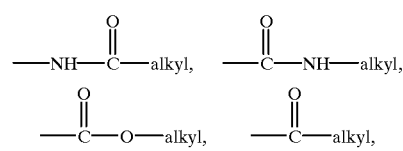

aryl, or heteroaryl wherein alkyl, aryl, and heteroaryl are defined as herein.

The term "cycloalkyl" means a saturated hydrocarbon ring which contains from 3 to 12 carbon atoms unless otherwise specified, for example, cyclopropyl, cyclobutyl, cyclopentyl, cyclohexyl, cycloheptyl, and adamantyl. The cycloalkyl ring may be unsubstituted or substituted by from 1 to 3 substituents selected from alkyl, cycloalkyl, cycloalkoxy, alkoxy, thioalkoxy all as defined herein, hydroxy, thiol, nitro, halogen, amino, mono and disubstituted amino, formyl, carboxyl, nitrile, alkylsulfoxyl, arylsulfoxyl, alkylsulfonyl, arylsulfonyl,

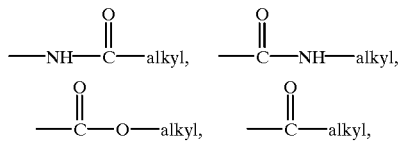

aryl, or heteroaryl wherein alkyl, aryl, and heteroaryl are defined as herein.

The terms "alkoxy" and "thioalkoxy" are O-alkyl or S-alkyl as defined above for alkyl.

Two alkoxy or thioalkoxy groups can be taken together to form a cyclic group such as

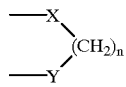

where X and Y are independently either O or S and n=1, 2, 3, or 4.

The term "aryl" means an aromatic radical which is a phenyl group, a benzyl group, a naphthyl group, a biphenyl group, a pyrenyl group, an anthracenyl group, or a fluorenyl group and the like, unsubstituted or substituted by 1 to 5 substituents selected from alkyl as defined above, alkoxy as defined above, thioalkoxy as defined above, hydroxy, thiol, nitro, halogen, amino, mono and disubstituted amino, formyl, carboxy, nitrile, arylsulfoxyl, alkylsulfoxyl, arylsulfonyl, alkylsulfonyl,

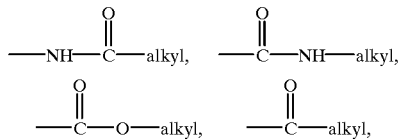

or heteroaryl wherein alkyl, aryl, and heteroaryl are defined as above.

The term "heteroaryl" means a heteroaromatic radical which is 2- or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, or 2-, 4-, 5-, 6-, or 7-benzoxazolyl, 2-, 4-, 5-, 6-, or 7-benzimidazolyl, 2-, 4-, 5-, 6-, or 7-benzothiazolyl, unsubstituted or substituted by 1 to 3 substituents selected from alkyl as defined above, aryl as defined above, alkoxy as defined above, thioalkoxy as defined above, hydroxy, thiol, nitro, halogen, formyl, amino, mono and disubstituted amino, carboxyl,

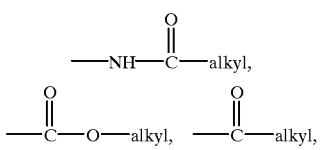

wherein alkyl is as defined above or phenyl.

"Halogen" is fluorine, chlorine, bromine or iodine.

Secondary amino is defined by a nitrogen with two groups attached, $R_a$—NH—$R_b$.

Tetiary amino is defined by a nitrogen with three groups attached, $R_a$—$NR_bR_c$.

The secondary and tertiary amino groups can occur as the immediate substitution or may be a substituent on any of the above defined groups.

Some of the compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, isethionic, and the like. Also contemplated are salts of amino acids such as arginate and the like and gluconate, galacturonate (see, for example, Berge, S. M., et al., "Pharmaceutical Salts," *Journal of Pharmaceutical Science*, 1977;66:1–19).

The acid addition salts of said basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge, S. M., et al., "Pharmaceutical Salts," *Journal of Pharmaceutical Science*, 1977;66:1–19).

The base addition salts of said acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof. In addition, some of the cyclic lactones of Formula I may exist in a tautomeric open chain keto-acid form, Formula II below, depending on the substitution pattern present at $R_1$, $R_2$, and $R_3$, or pH.

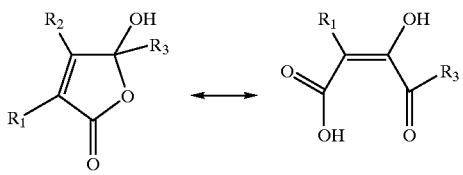

In such cases, the rate of equilibration may vary and activity may thus reside with either tautomer.

The compounds of Formula I are valuable antagonists of endothelin. The tests employed indicate that compounds of the invention possess endothelin antagonist activity. Thus, the compounds were tested for their ability to inhibit $[^{125}I]$-ET-1($[^{125}I]$-Endothelin-1) binding in a receptor assay. Selected compounds were also tested for antagonist activity by inhibition of ET-1 stimulated arachidonic acid release and ET-1 stimulated vasoconstriction.

The following radioligand binding assays were used (Reynolds E. E., Keiser J. A., Haleen S. J., Walker D. M., Davis L. S., Olszewski B., Taylor D. G., Hwang O., Welch K. M., Flynn M. A., Thompson D. M., et al., *J. Pharmacol. Exp. Ther.*, 1995;273:1410–1417).

The following cultured cells were used in binding experiments: CHO-K1 cells expressing recombinant human $ET_BR$ (HERBA B), or Ltk-cells expressing human $ET_AR$ (HERBA A). Each of these cell types expressed a homogeneous population of the designated ET receptor subtype, which displayed canonical $ET_AR$ or $ET_BR$ pharmacology. Membranes were prepared from cultured cells by lysing cells in cold lysis buffer (5 mM HEPES, 2 mM EDTA, pH 7.4) and homogenizing with a Dounce "A" homogenizer. All of the homogenates were centrifuged at 30,000× g for 20 minutes at 4° C. Membrane pellets were resuspended in cold buffer containing 20 mM Tris, 2 EM EDTA, 200 $\mu$M Pefablock, 10 $\mu$M phosphoramidon, 10 $\mu$M leupeptin, and 1 $\mu$M pepstatin (pH 7.4) and frozen at −80° C. until use. Radioligand and competing ligands were prepared in binding buffer containing 20 mM Tris, 2 mM EDTA, and 0.1% BSA.

Competition binding assays were initiated by combining membranes, $[^{125}I]$-ET-1 (40 pM) and competing ligand in a final volume of 250 $\mu$L and incubating for 2 hours at 37° C. The assay was terminated by filtration over Whatman GF/B filters that were presoaked with 50 mM Tris, pH 7.4, containing 0.2% BSA and 100 $\mu$M bacitracin. Nonspecific binding was defined as total binding minus nonspecific binding. Specific binding was analyzed by nonlinear least squared curve fitting (InPlot, GraphPad Software, San Diego, Calif.), and the estimated $IC_{50}$ value was used to calculate $K_i$ according to the method of Cheng and Prusoff (1973).

The following testing procedures were used (Doherty A. M., et al., "Design of C-Terminal Peptide Antagonists of Endothelin: Structure-Activity Relationships of ET-1 [16–21, D-His[16]]," *Bioorganic and Medicinal Chemistry Letters*, 1993;3:497–502).

Antagonist activity is measured by the ability of added compounds to reduce endothelin-stimulated arachidonic acid release in cultured vascular smooth muscle cells as arachidonic acid release (AAR). $[^3H]$Arachidonic Acid Loading Media (LM) is DME/F12+0.5% FCS×0.25 mCi/mL $[^3H]$arachidonic acid (Amersham). Confluent monolayers of cultured rabbit renal artery vascular smooth muscle cells were incubated in 0.5 mL of the LM over 18 hours, at 37° C., in 5% $CO_2$. The LM was aspirated, and the cells were washed once with the assay buffer (Hank's BSS+10 mM HEPES+fatty acid-free BSA [1 mg/mL], and incubated for 5 minutes with 1 mL of the prewarmed assay buffer. This solution was aspirated, followed by an additional 1 mL of prewarmed assay buffer, and further incubated for another 5 minutes. A final 5-minute incubation was carried out in a similar manner. The same procedure was repeated with the inclusion of 10 $\mu$L of the test compound (1 nM to 1 $\mu$M) and 10 $\mu$L ET-1 (0.3 nM), and the incubation was extended for 30 minutes. This solution was then collected, 10 $\mu$L of scintillation cocktail was added, and the amount of $[^3H]$ arachidonic acid was determined in a liquid scintillation counter.

Further functional antagonism is demonstrated by the in vitro antagonism of ET-1 stimulated vasoconstriction (VERA-A) in the rabbit femoral artery. This assay is run according to the following literature reference (Doherty A. M., Cody W. L.; He J. X., et al.). In vitro and in vivo studies with a series of hexapeptide endothelin antagonists. *J. Cardiovasc. Pharmacol.*, 1993:22(Suppl. 8):S98–102. The data are presented as pA2 values.

The data in Table I below shows the endothelin receptor binding and antagonists activity of representative compounds of the instant invention.

TABLE I

| Example | HERBA-A[a] | HERBA-B[a] | VERA-A[c] |
|---|---|---|---|
| 1 | >100 | >2500 | |
| 2 | 0.3 | 2300 | 6.9 |
| 3 | 2.0 | >2500 | |
| 4 | 1.0 | >2500 | 7.0 |
| 5 | 0.3 | >250 | |
| 6 | 2.0 | >2500 | |
| 7 | 1.0 | >2500 | |
| 9 | 180 | >25000 | |
| 10 | 0.6 | >2500 | 7.0 |
| 11 | 0.5 | >2500 | 6.2 |
| 12 | 0.2 | >250 | |
| 13 | 2.0 | >2500 | |
| 14 | 0.2 | 2300 | 6.9 |
| 16 | 2.0 | >2500 | — |
| 17 | 12.5 | >2500 | |
| 18 | 12 | >2500 | |
| 19 | 11.5 | 2200 | |
| 20 | 3.3 | 1600 | 6.2 |
| 21 | 2.0 | >2500 | — |
| 22 | 12 | >2500 | |
| 23 | 10 | >2500 | |
| 26 | 0.2 | 1900 | 7.8 |
| 27 | 14 | 3350 | |
| 28 | 12 | 4100 | |
| 29 | 40 | 17000 | |
| 30 | 180 | >2500 | |
| 31 | 2.0 | 2700 | |
| 32 | 4.0 | 900 | |
| 33 | 1.2 | 470 | 6.7 |
| 34 | 0.6 | 110 | |
| 35 | 1.0 | 210 | — |
| 36 | 2.0 | 300 | |
| 37 | 0.2 | 2300 | 6.9 |
| 38 | 1.0 | 800 | 7.0 |

[a]$IC_{50}$ values in nM
[b]Human cloned receptor data
[c]pA$_2$ values

As can be seen in Table I above, a representative compound of Formula I binds to the endothelin receptors $ET_A$ (HERBA-A) in the $\mu$M to nM range.

Table II presents representative examples displaying the excellent water solubility attained with these agents.

TABLE II

| Example | Aqueous Solubility |
|---------|--------------------|
| 11 | >25 mg/mL |
| 37 | >25 mg/mL |
| 26 | >80 mg/mL |

GENERAL SYNTHETIC APPROACHES

The compounds of Formula I may be prepared by several methods. In Scheme I, condensation of an aldehyde with an acetophenone-type compound in basic solution such as alcoholic sodium hydroxide. This gives a chalcone derivative which is treated with HCN in a solvent such as aqueous alcohol to give the nitrile. The nitrile is hydrolyzed to the ester with an acidic solution such as $HCl/MeOH/H_2O$. The ester is then condensed and cyclized with another aldehyde in a solvent such as methanol using a base such as sodium methoxide.

In Scheme II the chalcone from Scheme I is treated with the anion of triphenylorthothioformate in an organic solvent such as THF. This compound is then converted to a keto ester with a mix of mercury salts by warming in an alcoholic solvent such as ethanol. The keto ester can then be converted to compound, of Formula I as in Scheme I.

SCHEME I

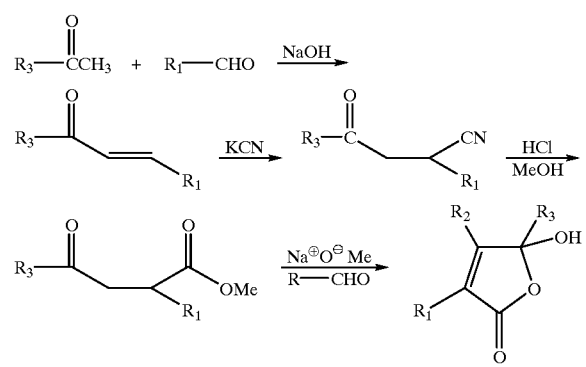

SCHEME II

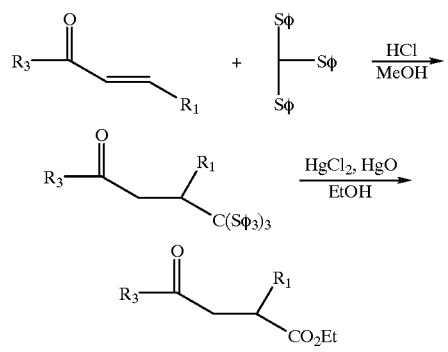

Additionally, the compounds of Formula I may be prepared by Scheme III. In Scheme III, a butenolide with a leaving group, such as halogen, mesylate, tosylate, or triflate, at either $R_1$, $R_2$, or $R_3$ ($R_2$ shown) is treated with a primary amine, secondary amine, or sodium sulfite to give a compound of Formula I, where Y' is a secondary amine, tertiary amine, or sulfonic acid.

SCHEME III

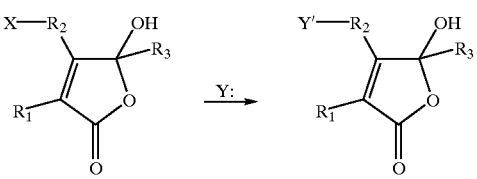

X = Leaving Group       Y: = primary amine, secondary amine, or sodium sulfite

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as antagonists of endothelin, the compounds utilized in the pharmaceutical method of this invention are administered at the initial dosage of about 0.01 mg to about 100 mg/kg daily. A daily dose range of about 0.01 mg to about 10 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting examples illustrate the methods for preparing the compounds of the invention.

EXAMPLE 1

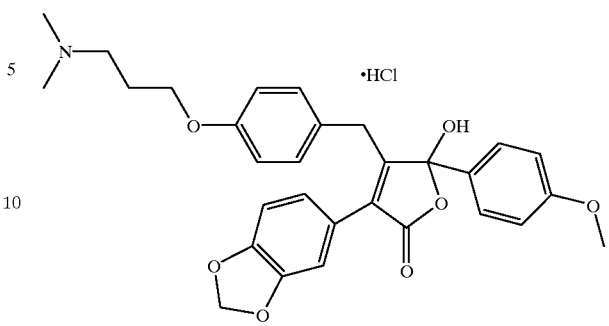

3-Benzo[1,3]dioxol-5-yl-4-[4-(3-dimethylamino-propoxy)-benzyl]-5-hydroxy-5-(4-methoxy-phenyl)-5H-furan-2-one.hydrocloride To methanol (12 mL) was added sodium metal (97 mg, 4.2 mmol) and stirred to dissolve. To this was added the ester, 2-Benzo[1,3]dioxol-5-yl-1-(4-methoxyphenyl)-4-oxo-butyric acid methyl ester (1.37 g, 4.0 mmol) then p-(3-dimethylaminopropoxy)benzaldehyde (870 mg, 4.0 mmol). The mixture was heated to reflux for 24 hours. The solution was then treated with acetic acid (2 mL) and refluxed an additional 24 hours. The solvents were removed by evaporation, and the residue was partitioned between ethyl acetate (50 mL) and water (100 mL). The organic phase was separated and dried over magnesium sulfate and evaporated to dryness. The crude product was then purified by flash chromatography (350 g silica gel, 15% MeOH/CH$_2$Cl$_2$). The butenolide was isolated by evaporation of the appropriate fractions to give 371 mg of a white foam. This was treated with 179 μL of 4N HCl in dioxane (0.717 mol) in dioxane (5 mL). The solution evaporated to a solid. The solid co-evaporated with ether to give a white foam, 395 mg (18%). The butenolide was identified by $^1$H NMR, IR, MS, [M+H]$^+$=518 Da., and microanalysis.

EXAMPLE 2

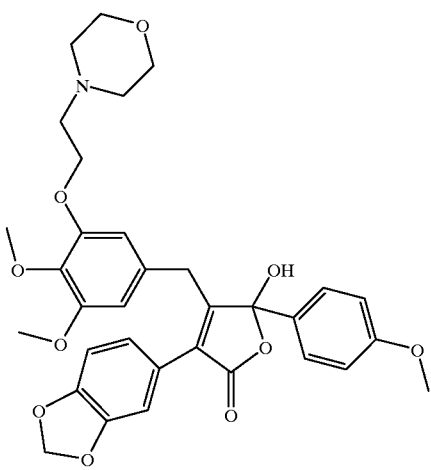

3-Benzol[1, 3]dioxol-5-yl-4-[3,4-dimethoxy-5(2-morpholin-4-yl-ethoxy)-benzyl]-5-hydroxy-5-(4-methoxy-phenyl)-5H-furan-2-one To methanol (10 mL) was added sodium metal (71 mg, 3.1 mmol) and stirred to dissolve. To this was added the ester, 2-Benzo[1,3]dioxol-5-yl-1-(4-methoxyphenyl)-4-oxo-butyric acid methyl ester (1.03 g, 3.0 mmol) then 3-(2-N-morpholinyl-ethoxy)-4,5-dimethoxy-benzaldehyde (0.92 g, 3.1 mmol). The mixture was heated to reflux for 24 hours. The solution was then treated with acetic acid (1 mL) and refluxed an additional 24 hours. The solvents were removed by evaporation, and the residue was partitioned between ethyl acetate (50 mL) and water (50 mL). The organic phase was separated and dried over magnesium sulfate and evaporated to dryness. The crude product was then purified by flash chromatography (125 g silica gel, 4% methanol/methylene chloride). The butenolide was isolated by evaporation of the appropriate fractions to give 350 mg (19%) as a white foam. The butenolide was identified by $^1$H NMR, IR, MS, [M+H]$^+$=606 Da. and microanalysis.

INTERMEDIATE 1

To ethanol (10 mL) was added sodium metal (97 mg, 4.2 mmol) and stirred to dissolve. To this was added the ester, 2-Benzo[1,3]dioxol-5-yl-1-(4-methoxyphenyl)-4-oxo-butyric acid methyl ester (1.37 g, 4.0 mmol) then 3-(ethylacetoxy)-4,5-dimethoxybenzaldehyde (1.10 g, 4.1 mmol). The mixture was heated to reflux for 18 hours. The solution was then treated with acetic acid (3 mL) and refluxed an additional 24 hours. The solvents were removed by evaporation, and the residue was partitioned between ethyl acetate (75 mL) and water (75 mL). The organic phase was separated and dried over magnesium sulfate and evaporated to dryness. The crude product was then purified by flash chromatography (150 g silica gel, 20% ethyl acetate-:methylene chloride). The butenolide was isolated by evaporation of the appropriate fractions to give 410 mg (18%) as an oil. The butenolide was identified by $^1$H NMR, IR, MS, [M+H]$^+$=579 Da., and microanalysis.

INTERMEDIATE 2

{5-[4-Benzo[1,3]dioxol-5-yl-2-(4-methoxy-phenyl)-5-oxo-2,5-dihydro-furan-3-ylmethyl]-2,3-dimethoxy-phenoxy}-acetic acid In methanol (15 mL) was dissolved the butenolide, Intermediate 1, and the solution treated with 1.010N sodium hydroxide (0.13 mL, 1.14 mmol), and the solution warmed to reflux for 24 hours. The mixture cooled to room temperature and evaporated free of methanol. The residue was partitioned between water (50 mL) and ether (50 mL). The aqueous phase was separated and washed with ether (50 mL) and ethyl acetate (50 mL). The aqueous phase was made acidic and extracted with fresh ethyl acetate (2×30 mL). The combined final extraction phases evaporated in vacuo to give an oil, 295 mg (94%). The butenolide was identified by $^1$H NMR, IR, MS, [M+H]$^+$=551 Da., and microanalysis.

EXAMPLE 3

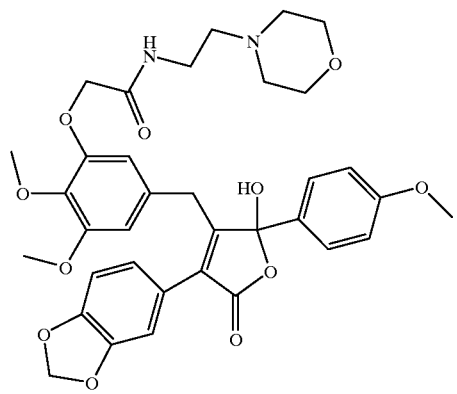

2-{5-[4-Benzo[1,3]dioxol-5-yl-2-hydroxy-2-(4-methoxy-phenyl)-5-oxo-2,5-dihydro-furan-3-ylmethyl]-2,3-dimethoxy-phenoxy}-N-(2-morpholin-4-yl-ethyl)-acetamide In DMF (8 mL) was dissolved the acid (Intermediate 2) (600 mg, 1.1 mmol), HOBT (162 mg, 1.2 mol), and DCC (248 mg, 1.2 mmol). To this was added N-2-aminoethyl-morpholine (156 mg, 1.2 mmol). The mixture stirred at room temperature overnight. The solution filtered free of insolubles and the filtrate evaporated to a paste. The paste dissolved in ethyl acetate (75 mL) and washed successively with water (100 mL) and brine (50 mL). The organic phase dried over MgSO$_4$ and evaporated in vacuo to give a foam. The foam was purified by flash chromatography (100 g flash silica gel, 2–5% methanol/methylene chloride). Evaporation of the appropriate fractions gave 430 mg (54%) of a white solid which was identified by $^1$H NMR, IR, MS, [M+H]$^+$= 663 Da., and microanalysis.

EXAMPLE 4

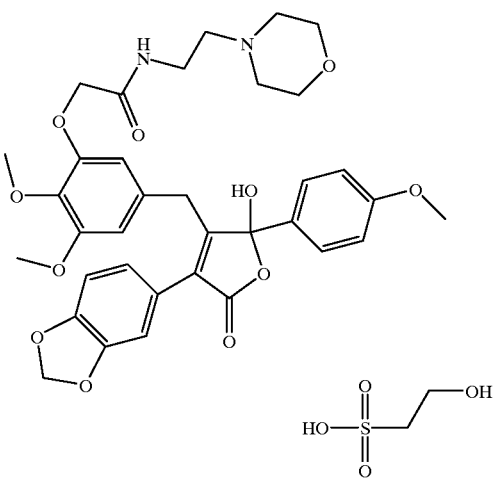

2-{5-[4-Benzo[1,3]dioxol-5-yl-2-hydroxy-2-(4-methoxy-phenyl])-5-oxo-2,5-dihydro-furan-3-ylmethyl]-2,3-dimethyl-phenoxy}-N-(2-morpholin-4-yl-ethyl)-acetamide 2-hydroxythanesulfonate In methanol (10 mL) was dissolved Example 3 (290 mg, 0.437 mmol) and isethionic acid (105 μL of 0.42N (aq.)

solution, 0.437 mmol). The residue stirred for 5 minutes and evaporated in vacua The residue triturated with ether (50 mL) and filtered to collect the solid, 340 mg (99%). The product was identified by $^1$H NMR, IR, MS, [M+H]$^+$=662 Da., and microanalysis.

EXAMPLE 5

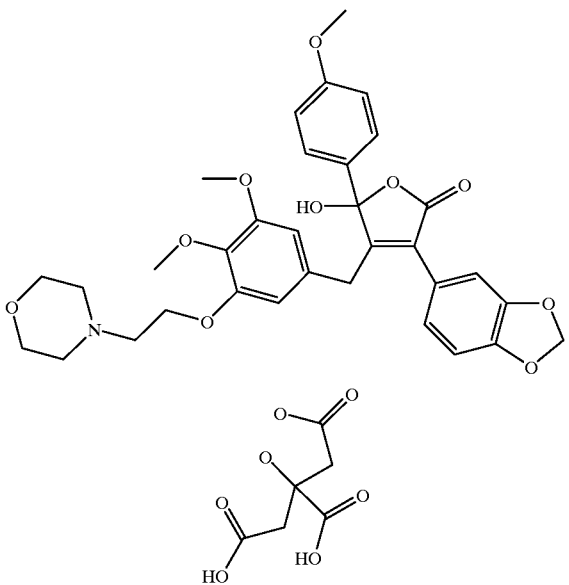

3-Benzo[1,3]-dioxol-5-yl-4-[3,4-dimethoxy-5-(2-morpholin-4-yl-ethoxy)-benzyl]-5-hydroxy-5-(4-methoxy-phenyl)-5H-furan-2-one 2-hydroxy-1,2,3-propanetricarboxylate (1:1)(salt)

In a manner similar to Example 4, Example 2 (135 mg, 0.223 mmol) was converted to the salt with citric acid (43 mg, 0.223 mmol). This gave 155 mg (87%) which was identified by $^1$H NMR, IR, MS, [M+H]$^+$=606 Da., and microanalysis.

EXAMPLE 6

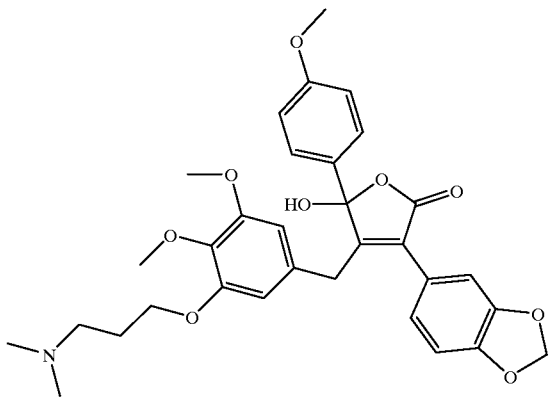

3-Benzo-[1,3]dioxol-5-yl-[3-(3-dimethylamino-propoxy)-4,5-dimethoxy-benzyl]-5-hydroxy-5-(4-methoxy-phenyl)-5H-furan-2-one To methanol (10 mL) was added sodium metal (71 mg, 3.1 mmol) and stirred to dissolve. To this was added the ester, 2-Benzo[1,3]dioxol-5-yl-1-(4-methoxyphenyl)-4-oxo-butyric acid methyl ester (1.03 g, 3.0 mmol) then 3-(3-dimethylamino)propoxy-4,5-dimethoxybenzaldehyde (829 mg, 3.1 mmol). The mixture was heated to reflux for 24 hours. The solution was then treated with acetic acid (1 mL) and refluxed an additional 24 hours. The solvents were removed by evaporation, and the residue was partitioned between very warm ethyl acetate (50 mL) and water (100 mL). The organic phase was separated and dried over magnesium sulfate and evaporated to dryness. The crude product was then purified by flash chromatography (120 g silica gel, 5–20% methanol/methylene chloride). The butenolide was isolated by evaporation of the appropriate fractions to give 75 mg (4%) as a white solid. The butenolide was identified by $^1$H NMR, IR, MS, [M+H]$^+$=578 Da., and microanalysis.

EXAMPLE 7

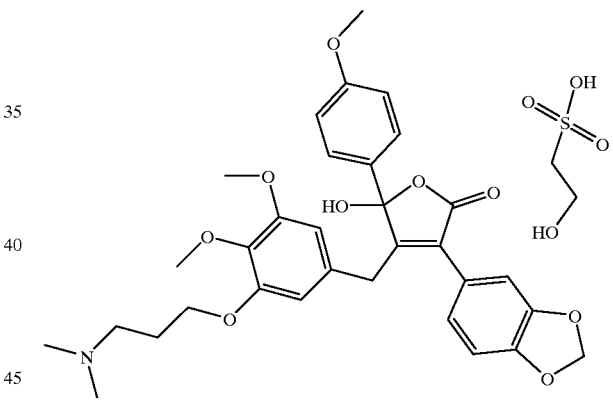

3-Benzo[1,3]dioxol-5-yl-4-[3-(3-dimethylaminopropoxy)-4,5-dimethoxy-benzyl]-5-hydroxy-5-(4-methoxy-phenyl)-5H-furan-2-one 2-hydroxyethanesulfonate In a manner similar to Example 4, Example 6 (312 mg, 0.540 mmol) was converted to the salt with isethionic acid (1.19 mL of 0.42N (aq.), 0.50 mmol). This gave 300 mg (85%) which was identified by $^1$H NMR, IR, MS, [M+H]$^+$= 578 Da., and microanalysis.

EXAMPLE 8

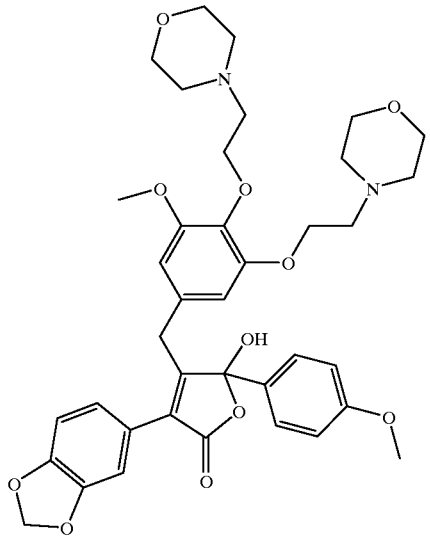

3-Benzo[1,3]dioxol-5-yl-5-hydroxy-4-[3-methoxy-4,
5-bis-(2-morpholin-4-yl-ethoxy)-benzyl]-5-(4-
methoxy-phenyl)-5H-furan-2-one To methanol (10 mL) was added sodium metal (45 mg, 1.95 mmol) and stirred to dissolve. To this was added the ester, 2-Benzo[1,3]dioxol-5-yl-1-(4-methoxyphenyl)-4-oxobutyric acid methyl ester (651 mg, 1.90 mmol) then 3,4-bis(2-N-morpholinylethoxy)-5-methoxy-benzaldehyde (780 mg, 1.97 mmol). The mixture was heated to reflux for 24 hours. The solution was then treated with acetic acid (1 mL) and refluxed an additional 24 hours. The solvents were removed by evaporation, and the residue was partitioned between ethyl acetate (100 mL) and water (50 mL). The organic phase was separated and dried over magnesium sulfate and evaporated to dryness. The crude product was then purified by flash chromatography (150 g silica gel, 10% methanol/methylene chloride). The butenolide was isolated by evaporation of the appropriate fractions to give 309 mg (44w) as a thick oil. The butenolide was identified by $^1$H NMR, IR, MS, [M+H]$^+$=704518 Da., and microanalysis.

EXAMPLE 9

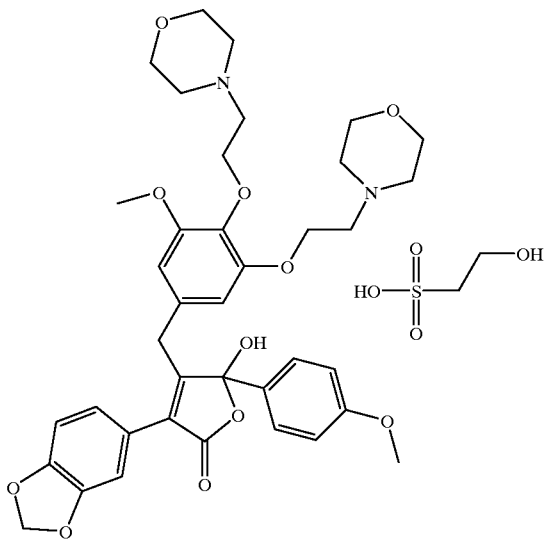

3-Benzo[1,3]dioxol-5-yl-5-hydroxy-4-[3-methoxy-4,
5-bis-(2-morpholin-4-yl-ethoxy)-benzyl]-5(4-
methoxy-phenyl)-5H-furan-2-one 2-
hydroxyethanesulfonate In a manner similar to Example 4, Example 8 (76 mg, 0.108 mmol) was converted to the salt with isethionic acid (0.514 mL of 0.42N (aq.), 0.216 mmol). This gave 160 mg (77%) which was identified by $^1$H NMR, IR, MS, [M+H]$^+$= 705 Da., and microanalysis.

EXAMPLE 10

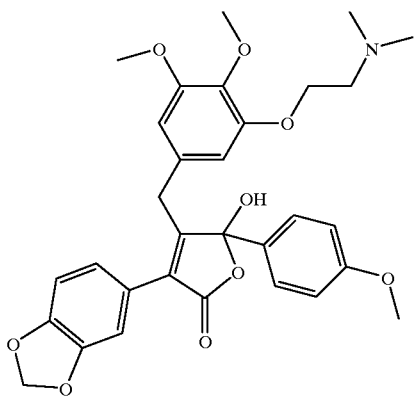

3-Benzo[1,3]dioxol-5-yl-4-[3-(2-dimethylamino-ethoxy)-4,5-dimethoxy-benzyl-]-5-hydroxy-5-(4-methoxy-phenyl)-5H-furan-2-one To methanol (10 mL) was added sodium metal (97 mg, 4.2 mmol) and stirred to dissolve. To this was added the ester, 2-Benzo[1,3]dioxol-5-yl-1-(4-methoxyphenyl)-4-oxo-butyric acid methyl ester (1.37 g, 4.0 mmol) then 3-(2-dimethylaminoethoxy-4,5-dimethoxybenzaldehyde (1.04 g, 4.1 mmol). The mixture was heated to reflux for 24 hours. The solution was then treated with acetic acid (1 mL) and refluxed an additional 24 hours. The solvents were removed by evaporation, and the residue was partitioned between warm ethyl acetate (75 mL) and water (50 mL). The organic phase was separated and dried over magnesium sulfate and evaporated to dryness. The crude product was then purified by flash chromatography (150 g silica gel, 10–15% methanol/methylene chloride). The butenolide was isolated by evaporation of the appropriate fractions to give 1.05 g (47%) as a white foam. The butenolide was identified by $^1$H NMR, IR, MS, [M+H]$^+$=564 Da., and microanalysis.

EXAMPLE 11

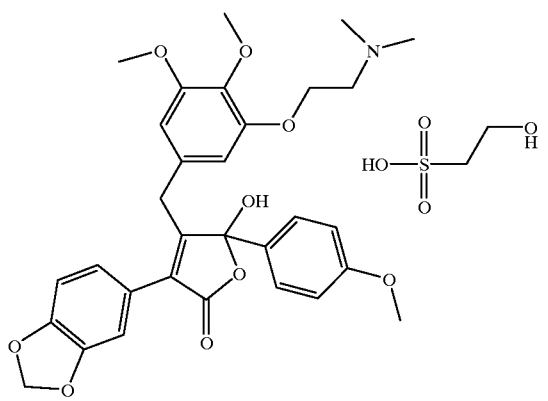

3-Benzo[1,3]dioxyl-5-yl-4-[3-(2-dimethylamino-ethoxy)-4,5-dimethoxy-benzyl]-5-hydroxy-5-(4-methoxy-phenyl)-5H-furan-2-one 2-hydroxyethanesulfonate In a manner similar to Example 4, Example 10 (363 mg, 0.644 mmol) was converted to the salt with isethionic acid (1.53 mL of 0.42N (aq.), 0.644 mmol). This gave 300 mg (68%) which was identified by $^1$H NMR, IR, MS, [M+H]$^+$=564 Da., and microanalysis.

EXAMPLE 12

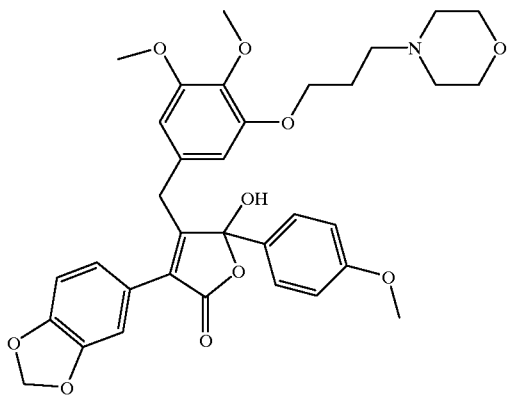

3-Benzo[1,3]dioxol-5-yl-4-[3,4-dimethoxy-5-(3-morphlin-4-yl-propoxy)-benzyl]-5-hydroxy-5-(4-methoxy-phenyl-)-5H-furan-2-one To methanol (10 mL) was added sodium metal (117 mg, 5.1 mmol) and stirred to dissolve. To this was added the ester, 2-Benzo[1,3]dioxol-5-yl-1-(4-methoxyphenyl)-4-oxo-butyric acid methyl ester (1.71 g, 5.0 mmol) then 3-(3-N-morpholinyl-propoxy)-4,5-dimethoxybenzaldehyde (1.55 g, 5.0 mmol). The mixture was heated to reflux for 24 hours. The solution was then treated with acetic acid (1 mL) and refluxed an additional 24 hours. The solvents were removed by evaporation, and the residue was partitioned between ethyl acetate (75 mL) and water (50 mL). The organic phase was separated and dried over magnesium sulfate and evaporated to dryness. The crude product was then purified by flash chromatography (150 g silica gel, 5% methanol/methylene chloride). The butenolide was isolated by evaporation of the appropriate fractions to give 560 mg (18%) as a foam. The butenolide was identified by $^1$H NMR, IR, MS, [M+H]$^+$=619 Da., and microanalysis.

EXAMPLE 13

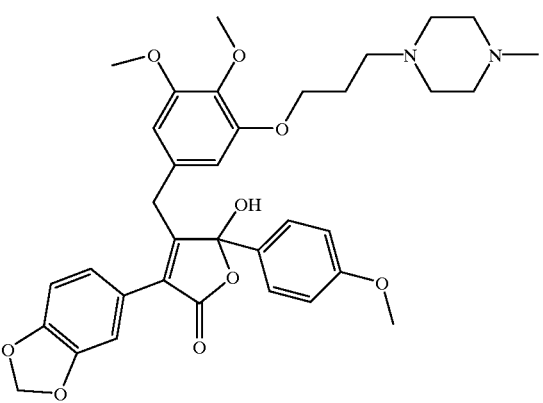

3-Benzo[1,3]dioxol-5-yl-4-{3,4-dimethoxy-5-[3-(4-methyl-piperazin-1-yl]-propoxy-benzyl}-5-hydroxy-5-(4-methoxy-phenyl)-5H-furan-2-one To methanol (10 mL) was added sodium metal (97 mg, 4.2 mmol) and stirred to dissolve. To this was added the ester, 2-Benzo[1,3]dioxol-5-yl-1-(4-methoxyphenyl)-4-oxo-butyric acid methyl ester (1.37 g, 4.0 mmol) then 3-((3-(N'-methyl)-N-piperazinyl)propoxy)-4,5-dimethoxybenzaldehyde (1.32 g, 4.1 mmol). The mixture was heated to reflux for 24 hours. The solution was then treated with acetic acid (1 mL) and refluxed an additional 24 hours. The solvents were removed by evaporation, and the residue was partitioned between ethyl acetate (100 mL) and water (50 mL). The organic phase was separated and dried over magnesium sulfate and evaporated to dryness. The crude product was then purified by flash chromatography (150 g silica gel, 5–20% methanol/methylene chloride). The butenolide was isolated by evaporation of the appropriate fractions to give 600 mg (24%) as a white foam. The butenolide was identified by $^1$H NMR, IR, MS, [M+H]$^+$= 633 Da., and microanalysis.

EXAMPLE 14

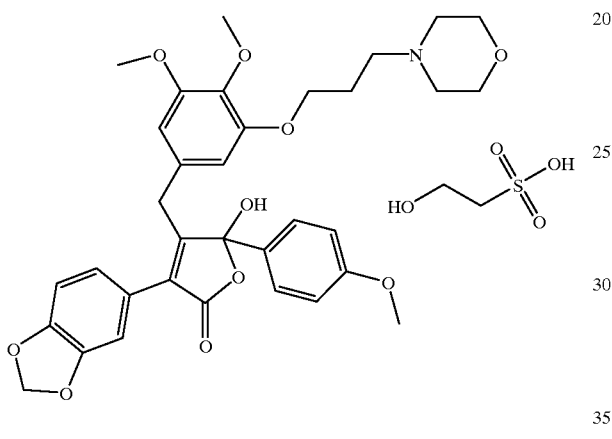

3-Benzo[1,3]dioxol-5-yl-4-{3,4-dimethoxy-5-[3-morpholin-4-yl-propoxy)-benzyl}5-hydroxy-5-(4-methoxy-phenyl)-5H-furan-2-one 2-hydroxyethanesulfonate In a manner similar to Example 4, Example 12 (360 mg, 0.581 mmol) was converted to the salt with isethionic acid (1.38 mL of 0.42N (aq.), 0.581 mmol). This gave 465 mg (100w) which was identified by $^1$H NMR, IR, MS, [M+H]$^+$= 619 Da., and microanalysis.

EXAMPLE 15

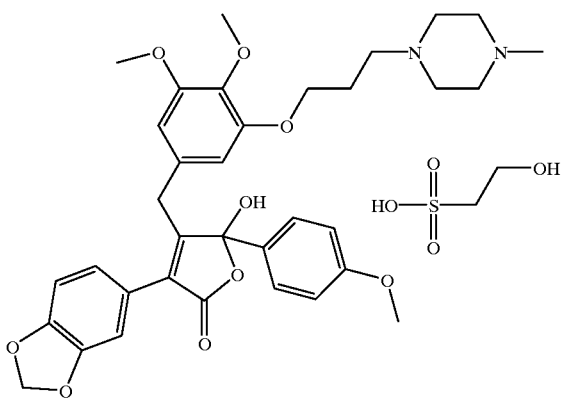

3-Benzo[1,3]dioxol-5-yl-4-{3,4-dimethoxy-5-[3-(4-methyl-piperazin-1-yl)-propoxyl-benzyl}-5-hydroxy-5-(4-methoxy-phenyl-5H-furan-2-one 2-hydroxyethanesulfonate In a manner similar to Example 4, Example 13 (430 mg, 0.679 mmol) was converted to the salt with isethionic acid (1.6 mL of 0.42N (aq.), 0.68 mmol). This gave 328 mg (64%) which was identified by $^1$H NMR, IR, MS, [M+H]$^+$= 633 Da., and microanalysis.

EXAMPLE 16

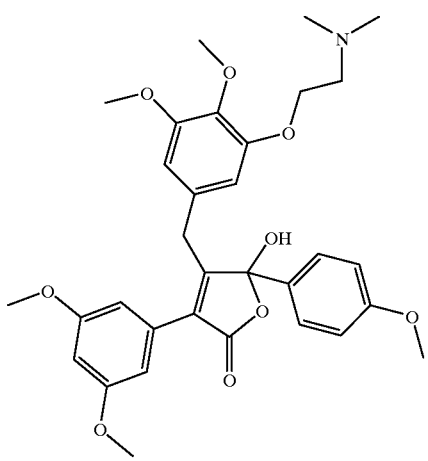

3-(3,5-Dimethoxy-phenyl])-4-[3-(2-dimethylamino-ethoxy)-4,5-dimethoxy-benzyl]-5-hydroxy-5-(4-methoxy-phenyl)-5H-furan-2-one To methanol (12 mL) was added sodium metal (42 mg, 1.84 mmol) and stirred to dissolve. To this was added the ester, 2-Benzo[1,3]dioxol-5-yl-1-(4-methoxyphenyl)-4-oxo-butyric acid methyl ester (649 mg, 1.81 mmol) then 3-(3-dimethylamino)propoxy-4,5-dimethoxy-benzaldehyde (460 mg, 1.81 mmol). The mixture was heated to reflux for 24 hours. The solution was then treated with acetic acid (1 mL) and refluxed an additional 24 hours. The solvents were removed by evaporation, and the residue was partitioned between ethyl acetate (100 mL) and water (60 mL). The organic phase was separated and dried over magnesium sulfate and evaporated to dryness. The crude product was then purified by flash chromatography (150 g silica gel, 10–20% methanol/methylene chloride). The butenolide was isolated by evaporation of the appropriate fractions to give 385 mg (37%) as a foam. The butenolide was identified by $^1$H NMR, IR, MS, [M+H]$^+$=580 Da., and microanalysis.

EXAMPLE 17

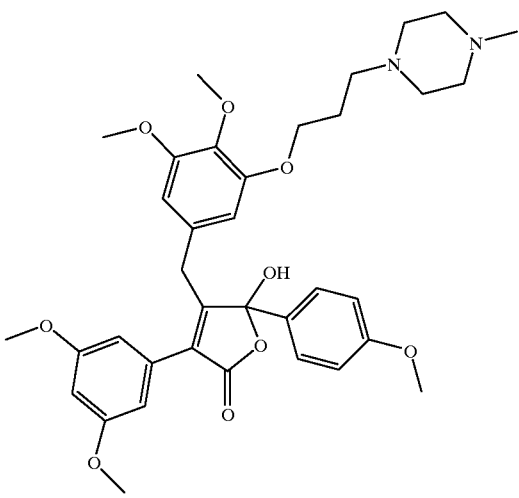

4-{3,4-Dimethoxy-5-[3-(4-methyl-piperazzin-1-yl)-propoxy]-benzyl}-3-(3,5-dimethoxy-phenyl)-5-hydroxy-5-(4-methoxy-phenyl)-5-hydroxy-5-(4-methoxy-phenyl)-5H-furan-2-one To methanol (12 mL) was added sodium metal (74 mg, 3.2 mmol) and stirred to dissolve. To this was added the ester, 2-Benzo[1,3]dioxol-5-yl-1-(4-methoxyphenyl)-4-oxo-butyric acid methyl ester (1.11 g, 3.1 mmol) then 3-((3-(N'-methyl)-N-piperazinyl)propoxy)-4,5-dimethoxybenzaldehyde (1.0 g, 3.1 mmol). The mixture was heated to reflux for 24 hours. The solution was then treated with acetic acid (2 mL) and refluxed an additional 24 hours. The solvents were removed by evaporation, and the residue was partitioned between ethyl acetate (100 mL) and water (60 mL). The organic phase was separated and dried over magnesium sulfate and evaporated to dryness. The crude product was then purified by flash chromatography (125 g silica gel, 15–20% methanol/methylene chloride). The butenolide was isolated by evaporation of the appropriate fractions to give 840 mg (42%) as a foam. The butenolide was identified by $^1$H NMR, IR, MS, [M+H]$^+$=648 Da., and microanalysis.

EXAMPLE 18

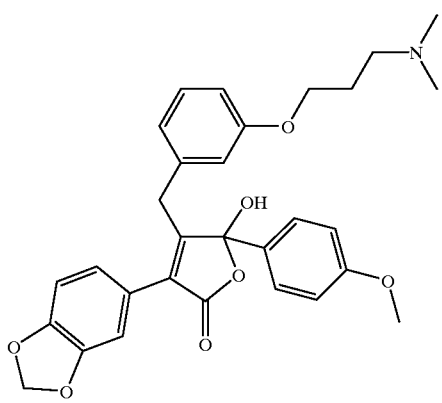

3-Benzo[1,3]dioxol-5-yl-4-[3-(3-dimethylamino-propoxy)-benzyl]-5-hydroxy-5-(4-methoxy-phenyl)-5H-furan-2-one To methanol (50 mL) was added sodium metal (0.89 g, 38.7 mmol) and stirred to dissolve. To this was added the ester, 2-Benzo[1,3]dioxol-5-yl-1-(4-methoxyphenyl)-4-oxo-butyric acid methyl ester (10.61 g, 31.0 mmol) then 3-(3-dimethylaminopropoxy)-benzaldehyde (8.03 g, 38.7 mmol). The mixture was heated to reflux for 5 hours. The solution was then treated with acetic acid (6.3 mL) and refluxed an additional 15 hours. The solvents were removed by evaporation, and the residue was partitioned between warm ethyl acetate (250 mL) and water (50 mL). The organic phase was separated and dried over magnesium sulfate and evaporated to dryness. The crude product was then purified by flash chromatography (silica gel, 5% EtOAc in CH$_2$Cl$_2$). The butenolide was isolated by evaporation of the appropriate fractions to give 10.61 g (66.1%) as a white foam. The butenolide was identified by $^1$H NMR, IR, MS, [M+H]$^+$=518 Da., and microanalysis.

EXAMPLE 19

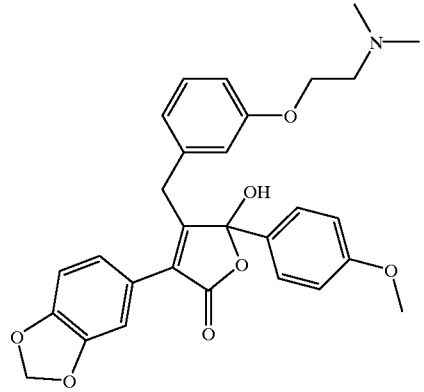

3-Benzo[1,3]dioxol-5-yl-4-[3-(2-dimethylamino-ethoxy)-benzyl]-5-hydroxy-5-(4-methoxy-phenyl)-5H-furan-2-one To methanol (50 mL) was added sodium metal (0.84 g, 36.5 mmol) and stirred to dissolve. To this was added the ester, 2-Benzo[1,3]dioxol-5-yl-1-(4-methoxyphenyl)-4-oxo-butyric acid methyl ester (10.00 g, 29.2 mmol) then 3-(2-dimethylaminoethoxy)-benzaldehyde (7.06 g, 36.5 mmol). The mixture was heated to reflux for 5 hours. The solution was then treated with acetic acid (6.3 mL) and refluxed an additional 15 hours. The solvents were removed by evaporation, and the residue was partitioned between warm ethyl acetate (250 mL) and water (50 mL). The organic phase was separated and dried over magnesium sulfate and evaporated to dryness. The crude product was then purified by flash chromatography (silica gel, 5% EtOAc/CH$_2$Cl$_2$). The butenolide was isolated by evaporation of the appropriate fractions to give 4.30 g (29%) as a white foam. The butenolide was identified by $^1$H NMR, IR, MS, [M+H]$^+$=504 Da., and microanalysis.

EXAMPLE 20

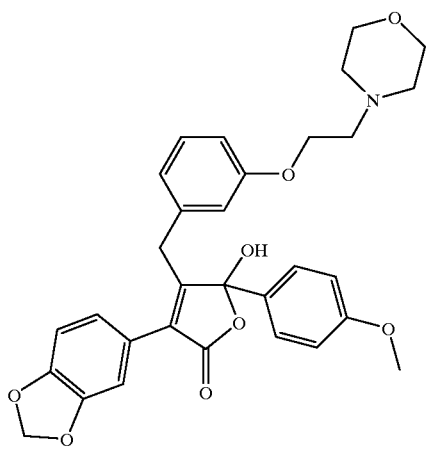

3-Benzo[1,3]dioxol-5-yl-5-hydroxy-5-(methyl-phenyl)-4-[3-(2-morpholin-4-yl-ethoxy)-benzyl]-5H-furan-2-one To methanol (50 mL) was added sodium metal (0.84 g, 36.5 mmol) and stirred to dissolve. To this was added the ester, 2-Benzo[1,3]dioxol-5-yl-1-(4-methoxyphenyl)-4-oxo-butyric acid methyl ester (10.00 g, 29.2 mmol) then 3-(2-morpholinoethoxy)-benzaldehyde (8.60 g, 36.5 mmol). The mixture was heated to reflux for 5 hours. The solution was then treated with acetic acid (6.3 mL) and refluxed an additional 15 hours. The solvents were removed by evaporation, and the residue was partitioned between warm ethyl acetate (250 mL) and water (50 mL). The organic phase was separated and dried over magnesium sulfate and evaporated to dryness. The crude product was then purified by flash chromatography (silica gel, 5% EtOAc/CH$_2$Cl$_2$). The butenolide was isolated by evaporation of the appropriate fractions to give 12.00 g (75%) as a creamy foam. The butenolide was identified by $^1$H NMR, IR, MS, [M+H]$^+$=546 Da., and microanalysis.

EXAMPLE 21

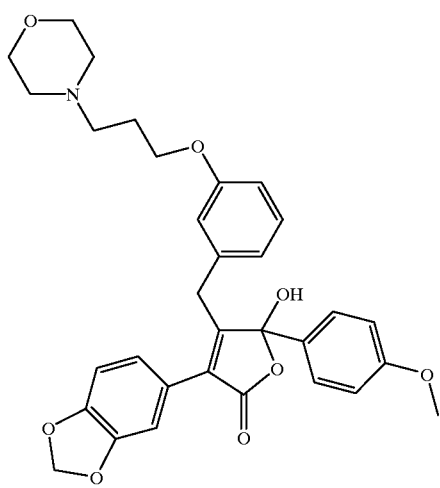

3-Benzo[1,3]dioxol-5-yl-5-hydroxy-5-(4-methoxy-phenyl)-4-[3-(3-morpholin-4-yl-propoxy)-benzyl]-5H-furan-2-one To methanol (20 mL) was added sodium metal (322 mg, 14.00 mmol) and stirred to dissolve. To this was added the ester, 2-Benzo[1,3]dioxol-5-yl-1-(4-methoxyphenyl)-4-oxo-butyric acid methyl ester (4.37 g, 12.76 mmol) then 3-(3-morpholinopropoxy)benzaldehyde (3.18 g, 12.76 mmol). The mixture was heated to reflux for 5 hours. The solution was then treated with acetic acid (2.8 mL) and refluxed an additional 15 hours. The solvents were removed by evaporation. The residue was stirred in EtOAc (150 mL) and then water (100 mL). White solid was collected by filtration, washed again with H$_2$O, followed by Et$_2$O with a little THF. Dry in vacuum to give 3.05 g of the desired compound (43%). The butenolide was identified by $^1$H NMR, IR, MS, [M+H]$^+$=560 Da., and microanalysis.

EXAMPLE 22

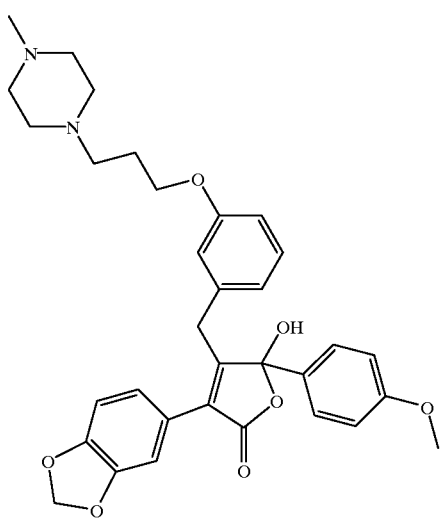

3-Benzo[1,3]dioxol-5-yl-5-hydroxy-5-(4-methoxy-phenyl)-4-{3-[3-(4-methyl-piperazin-1-yl)-propoxy]-benzyl}-5H-furan-2-one To methanol (10 mL) was added sodium metal (132 mg, 5.74 mmol) and stirred to dissolve. To this was added the ester, 2-Benzo[1,3]dioxol-5-yl-1-(4-methoxyphenyl)-4-oxo-butyric acid methyl ester (1.57 g, 4.58 mmol) then 3-(3-(4-methylpiperazino)propoxy)-benzaldehyde (1.20 g, 4.5 mmol). The mixture was heated to reflux for 5 hours. The solution was then treated with acetic acid (0.75 mL) and refluxed an additional 15 hours. The solvents were removed by evaporation, and the residue was partitioned between warm ethyl acetate (100 mL) and water (30 mL). The organic phase was separated and dried over magnesium sulfate and evaporated to dryness. The crude product was then purified by flash chromatography (silica gel, 10% MeOH/CH$_2$Cl$_2$). The butenolide was isolated by evaporation of the appropriate fractions to give 1.55 g (459) as a white foam. The butenolide was identified by $^1$H NMR, IR, MS, [M+H]$^+$=573 Da., and microanalysis.

EXAMPLE 23

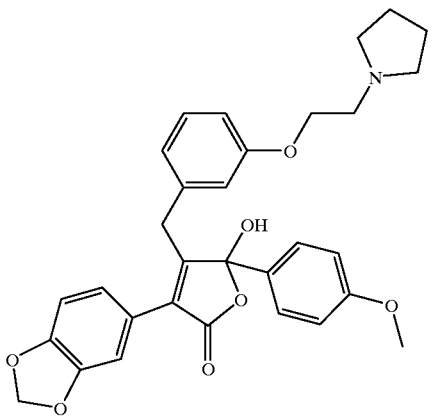

3-Benzo[1,3]dioxol-5-yl-5-hydroxy-5-(4-methoxy-phenyl)-4-[3-(2-pyrrolidin-1-yl-ethoxy)-benzyl]-5H-furan-2-one To methanol (15 mL) was added sodium metal (210 mg, 9.13 mmol) and stirred to dissolve. To this was added the ester, 2-Benzo[1,3]dioxol-5-yl-1-(4-methoxyphenyl)-4-oxo-butyric acid methyl ester (2.50 g, 7.30 mmol) then 3-(2-pyrrolidinoethoxy)benzaldehyde (2.00 g, 9.12 mmol). The mixture was heated to reflux for 5 hours. The solution was then treated with acetic acid (1.2 mL) and refluxed an additional 15 hours. The solvents were removed by evaporation, and the residue was partitioned between warm ethyl acetate and water. The organic phase was separated and dried over magnesium sulfate and evaporated to dryness. The crude product was then purified by flash chromatography (silica gel, 3–5% MeOH/CH$_2$Cl$_2$). The butenolide was isolated by evaporation of the appropriate fractions to give 2.46 g (64%) as a white powder. The butenolide was identified by IH NMR, IR, MS, [M+H]$^+$=530 Da., and microanalysis

INTERMEDIATE 3

To 4-methoxyacetophenone 2.20 g (14.1 mmol) in absolute ethanol (7.0 mL) in an erlenmeyer was added 3-methoxy-5-(2-dimethylaminoethoxy)benzaldehyde 2.92 g (13.1 mmol) in absolute ethanol (3.0 mL). The solution was stirred while 10% sodium hydroxide (0.45 mL) added. The mixture was stirred for 4 hours. The solvent was evaporated and the residue partitioned between ethyl acetate (50 mL) and water (50 mL). The organic phase was separated and the aqueous extracted with additional ethyl acetate (50 mL). The organic layers were combined, dried over magnesium sulfate, and evaporated in vacuo to a red oil which was flash chromatographed on silica gel (2% methanol/chloroform) to give the chalcone 4.03 g (896%) as a yellow oil which was identified by $^1$H NMR and MS.

INTERMEDIATE 4

To the chalcone, Intermediate 3, 4.03 g (11.3 mmol) in 2-ethoxyethanol (15 mL) was added acetic acid (0.78 mL) and the solution heated to 110° C. Potassium cyanide 1.08 g (16.6 mmol) in water (4 mL) was slowly added, and the solution was stirred at 110° C. for 45 minutes. The solution was cooled and the solvent evaporated. The residue was partitioned between ethyl acetate (75 mL) and water (75 mL). The organic layer was separated, and the aqueous was extracted with ethyl acetate (2×75 mL). Combined organic layers, dried over magnesium sulfate and evaporated to a dark yellow oil. $^1$H NMR indicated unreacted chalcone was present. The reaction was repeated as above with acetic acid (1.40 mL) and potassium cyanide 2.20 g (34.0 mmol). Heated 30 minutes and worked up as above to give the nitrile as a brown oil 4.76 g (>100%). The nitrile was identified by $^1$H NMR and MS. The product was used without purification in the preparation of the ester.

INTERMEDIATE 5

To the crude nitrile, Intermediate 4, (11.3 mmol) was added methanol/p-dioxane (60/40, 40 mL) followed by the addition of p-toluenesulfonic acid 2.15 g (11.3 mmol). The solution was heated to reflux for 18 hours. Additional p-toluenesulfonic acid 4.30 g (22.6 mmol) was added and the heating continued for 6 hours. The solution was cooled and the solvent evaporated. The residue was dissolved in ethyl acetate (100 mL) and washed with saturated sodium bicarbonate (2×100 mL). The organic layer was dried over magnesium sulfate and evaporated to give the ester 3.20 g (68% based on chalcone) as a red oil which was identified by $^1$H NMR and MS.

EXAMPLE 24

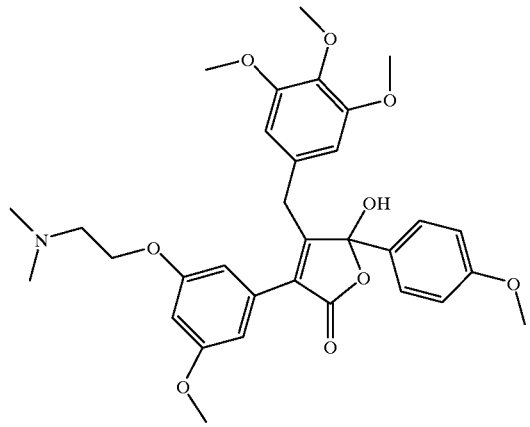

3-[3-(2-Dimethylamino-ethoxy)-5-methoxy-phenyl]-5-hydroxy5-(4-methoxy-phenyl)-4-(3,4,5-trimethoxy-benzyl)-5H-furan-2-one To methanol (20 mL) was added sodium metal 0.194 g (8.43 mmol) and stirred to dissolve. To this solution was added the ester, Intermediate 5, 3.20 g (7.70 mmol) followed by 3,4,5-trimethoxybenzaldehyde 1.89 g (9.63 mmol). The mixture was heated to reflux for 24 hours. The solution was then treated with acetic acid (2.0 mL) and refluxed an additional 20 hours. The solvent was removed by evaporation, and the residue was partitioned between ethyl acetate (100 mL) and water (100 mL). Adjusted pH to 9.5 (5% NaOH) and removed organic layer. The aqueous layer was adjusted to pH 7.0 (2 M HCl) and then extracted with ethyl acetate (2×100 mL). The organic layers were combined, dried over magnesium sulfate, and evaporated to give a yellow foam which was flash chromatographed on silica gel 100 g (2–10% methanol/chloroform) to give the butenolide 0.67 g (15%) as a light yellow foam which was identified by 1H NMR, MS, [M+H]$^+$=580 Da. and microanalysis.

EXAMPLE 25

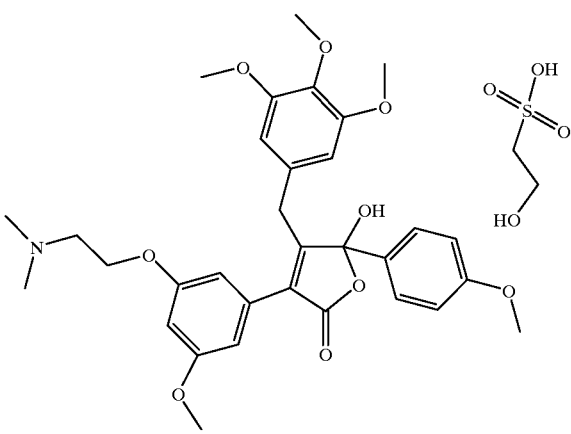

3-[3-(2-Dimethylamino-ethoxy)-5-methoxy-phenyl]-
5-hydroxy-5-(4-methoxy-phenyl)-4-(3,4,5-
trimethoxy-benzyl)-5H-furan-2-one
2hydroxyethanesulfonate In a manner similar to Example 4, Example 24 (490 mg, 0.85 mmol) was converted to the salt with isethionic acid (2.00 mL of 0.42N (aq.), 0.84 mmol). This gave 530 mg (90%) which was identified by $^1$H NMR, MS, [M+H]$^+$=580 Da., and microanalysis.

INTERMEDIATE 6

Sodium metal 0.449 g (19 mmol) was dissolved in absolute anhydrous ethanol (50 mL). To the solution was added 3-hydroxy-4,5-dimethoxybenzaldehyde 3.49 g (19 mmol), followed by a solution of 1,3-propane sultone 2.33 g (19 mmol) in ethanol (20 mL). The mixture was heated to reflux for 1.5 hours giving a solid. The solid was filtered, washed with ethanol and ethyl ether, and dried in vacuo, 5.67 g, 91%, which was identified by $^1$H NMR, MS, and microanalysis.

EXAMPLE 26

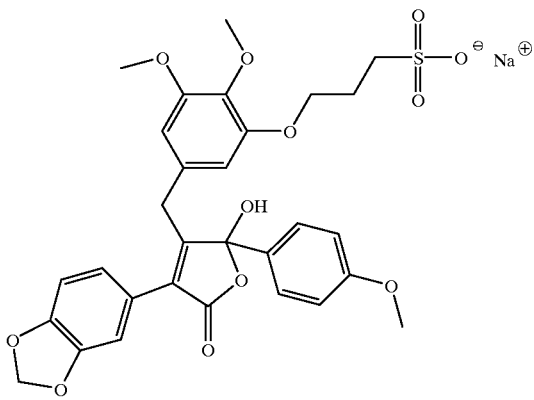

Sodium, 5-{5-[4-Benzo[1,3]dioxol-5-yl-2-hydroxy-2
(4-methoxy-phenyl)-5-oxo)-2,5-dihydro-furan-3-
ylmethyl]2,3-dimethoxy-phenoxy}-propane-1-
sulfonate To methanol 50 mL was added sodium metal 0.27 g (11.80 mmol) and stirred to dissolve. To this was added the ester, 2-Benzo[1,3]dioxol-5-yl-1-(4-methoxyphenyl)-4-oxo-butyric acid methyl ester, 3.85 g (11.25 mmol) then (12.93 mmol). The mixture was heated to reflux for 16 hours. The solution was then treated with acetic acid (5 mL) and refluxed an additional 16 hours. The solvents were removed by evaporation, and the residue was partitioned between ether (100 mL) and water (50 mL). The aqueous phase was acidified with 8N HCl, giving an oily precipitate. The oil was separated and purified by chromatography on silica gel (50 g), eluted with 20% methanol in chloroform. A solid was recovered by addition of ethyl ether to the concentrate of the appropriate fractions, 0.697 g (9.7%). The butenolide was recovered as the 1/3 Na. salt and identified by $^1$H NMR, MS, [M+H]$^+$=613.3 Da., and microanalysis.

The following compounds are prepared in a similar manner: 3-{5-[4-Benzo[1,3]dioxol-5-yl-2-hydroxy-2-(4-methoxy-phenyl)-5-oxo-2,5-dihydro-furan-3-ylmethyl]-2,3-dimethoxy-phenoxy}-butane-1-sulfonic acid; 3-{5-[4-Benzo[1,3]dioxol-5-yl-2-hydroxy-2-(4-methoxy-phenyl)-5-oxo-2,5-dihydro-furan-3-ylmethyl]-2,3-dimethoxy-phenoxy}-ethane-1-sulfonic acid; and 3-{5-[4-Benzo[1,3]dioxol-5-yl-2-hydroxy-2-.(4-methoxy-phenyl)-5-oxo-2,5-dihydro-furan-3-ylmethyl]-2,3-dimethoxy-phenoxy}-pentane-1-sulfonic acid.

INTERMEDIATE 7

To 2-hydroxy-4-methoxyacetophenone 20 g (120 mmol) in dimethyl formamide (250 mL) was added cesium carbonate 97.6 g (299 mmol) and 3-chloropropyl-dimethylamine hydrochloride 31.6 g (200 mmol). The solution was warmed to 90° C. for 3.5 hours followed by stirring at 25° C. for 48 hours. The mixture was filtered and evaporated to an oil in vacuo. The oil was partitioned between ethyl ether and water, and the ether phase was extracted with 2N HCl. The acid extract was layered with ethyl ether, and the pH of the aqueous phase was adjusted to 14 with 25% sodium hydroxide solution. The organic phase was washed with brine, dried over magnesium sulfate, filtered, and evaporated in vacuo to an oil, 22.04 g (73%), which was identified by $^1$H NMR, MS, and microanalysis.

INTERMEDIATE 8

To 3,4-methylenedioxybenzaldehyde 10.7 g (71.3 mmol) in absolute ethanol (100 mL) in an erlenmeyer was added Intermediate 7, 17.92 g (71.3 mmol). The solution was warmed while 12.5% sodium hydroxide (10 mL) added. The mixture was refluxed for 2 hours and evaporated in vacuo to an oil. The mixture was partitioned between ethyl ether and 1N HCl. The organic phase was separated and the pH of the aqueous phase was adjusted to 9 with 6N sodium hydroxide. The aqueous phase was extracted with ethyl ether, which was washed with brine, dried over anhydrous magnesium sulfate, filtered, and evaporated in vacuo to an oil, 25.99 g (95%), which was identified by $^1$H NMR, MS, and microanalysis.

INTERMEDIATE 9

To the chalcone, Intermediate 8, 25.87 g (67 mmol) in 2-ethoxyethanol (100 mL) at 80° C. was added acetic acid (8.86 g) followed by slow addition of potassium cyanide 13.75 g (211 mmol) in water 20 mL. The solution was stirred at 120° C. for 0.5 hours. The solution was cooled over 18 hours giving a solid. The solid was filtered, washed with 50/50 ethanol/water followed by washing with ethyl ether. The solid was dried in vacuo, 229 (79%). The nitrile was identified by $^1$H NMR, MS, and microanalysis.

INTERMEDIATE 10

To the nitrile, Intermediate 9, 21.75 g (53.1 mmol) was added methanol (180 mL) and dioxane (120 mL). To the mixture was added p-toluenesulfonic acid monohydrate 29.1 g (153 mmol). The mixture was heated to reflux for 48 hours and evaporated to a glassy solid. The residue was suspended in ethyl acetate and washed with saturated sodium bicarbonate solution and brine. The organic phase was washed with brine, dried over magnesium sulfate, and evaporated in vacuo to a small volume. The residue was triturated with ethyl ether, giving a solid which was then filtered and dried in vacuo, 18.43 g (78%), identified by $^1$H NMR, MS, and microanalysis.

INTERMEDIATE 11

To 3,4-methylenedioxybenzaldehyde 7.51 g (50 mmol) in absolute ethanol (50 mL) in an erlenmeyer was added 4-hydroxyacetophenone 6.81 g (50 mmol). The solution was warmed while 12.5% sodium hydroxide (20 mL) added. The mixture was refluxed for 1 hour and allowed to stand overnight at 25° C. The pH was adjusted to 4 with 6N HCl, giving a precipitate. The solid was collected by filtration and washed with water. The solid was dissolved in ethyl acetate, washed with brine, and dried over anhydrous magnesium sulfate. The solution was evaporated in vacuo to a small volume, and the product was precipitated by addition of petroleum ether. The solid was filtered and dried in vacuo giving 9.25 g of a yellow solid, mp 200–204° C., which was identified by $^1$H NMR, MS, and microanalysis.

INTERMEDIATE 12

To the chalcone, Intermediate 11, 8.0 g (29.8 mmol) in dimethylformamide (75 mL) was added cesium carbonate 46 g (144 mmol) followed by addition of 2-chloroethylmorpholine 7.95 g (69.0 mmol). After heating at 90° C. for 2 hours, the mixture solidified. The paste was filtered, washed with dimethylformamide, and the filtrates were evaporated to a solid in vacuo. The solid was dissolved in ethyl acetate, and washed with iN NaOH, and brine. The organic phase was dried over magnesium sulfate, filtered, and evaporated in vacuo to a small volume giving a precipitate. The paste was filtered, washed with ethyl ether, and dried in vacuo giving a solid, 9.0 g, mp 125–126° C. The chalcone was identified by $^1$H NMR, MS, and microanalysis.

INTERMEDIATE 13

To the chalcone, Intermediate 12, 8.75 g (22.9 mmol) in 2-ethoxyethanol (45 mL) at 80° C. was added acetic acid (3.02 g) followed by slow addition of potassium cyanide 4.68 g (71.8 mmol) in water (10 mL). The solution was stirred at 120° C. for 0.5 hours. The solution was cooled over 1 hour and evaporated to an oil. The oil was suspended in ethyl ether, and extracted with water. The water extract was adjusted to pH 13 with 1N sodium hydroxide solution and extracted exhaustively with ethyl acetate. The organic phase was washed with brine, dried over magnesium sulfate, filtered, and evaporated in vacuo to an oil, 10.9 g (74%). The nitrile was identified by $^1$H NMR, MS, and microanalysis.

INTERMEDIATE 14

To the nitrile, Intermediate 13, 10.8 g (22.0 mmol) was added methanol (75 mL) and dioxane (75 mL). To the mixture was added p-toluenesulfonic acid monohydrate 12 g (63.1 mmol). The mixture was heated to reflux for 48 hours and evaporated to a glassy solid. The residue was suspended in ethyl acetate and washed with saturated sodium bicarbonate solution and brine. The organic phase was extracted with 1N HCl which was separated from the organic phase. The acid extract was then extracted with ethyl acetate, while the mixture was made basic by the addition of saturated sodium bicarbonate. The organic phase was washed with brine, dried over magnesium sulfate, and evaporated in vacuo to a small volume. The residue was triturated with a mixture of ethyl ether and petroleum ether, giving a solid which was then filtered and dried in vacuo, 6.62 g, identified by $^1$H NMR, MS, and microanalysis.

EXAMPLE 27

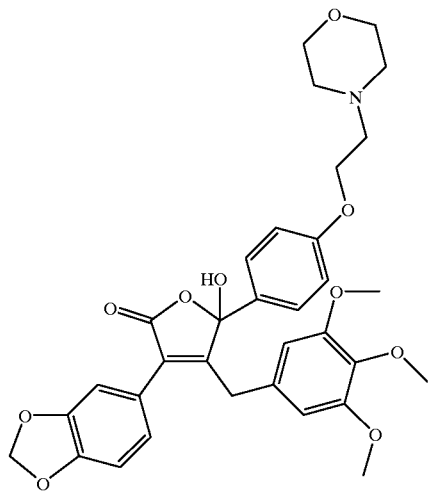

3-Benzo[1,3]dioxol-5-yl-5-hydroxy-5-[4-(2-morpholin-4-ethoxy)-phenyl]-4-(3,4,5-trimethoxy-benzyl)-5H-furan-2-one To methanol (45 mL) was added sodium metal, 0.217 g (9.44 mmol) and stirred to dissolve. To this was added the ester, Intermediate 14, (3.97 g, 9.0 mmol) then 3,4,5-trimethoxybenzaldehyde, 2.19 g (11.19 mmol). The mixture was heated to reflux for 18 hours. The solution was then treated with acetic acid (5 mL) and refluxed an additional 15 hours. The solvents were removed by evaporation, and the residue was partitioned between ether (100 mL) and 1 sodium hydroxide (100 mL). The aqueous phase was separated and acidified with 6N HCl. This acidic solution was extracted with 100 mL ethyl ether. The organic phase was separated, washed with brine, dried over magnesium sulfate, and evaporated in vacuo. This gave the butenolide 3.13 g (57%) as a solid. The butenolide was identified by 1H NMR, MS, [M+H]$^+$=606 Da., and microanalysis.

EXAMPLE 28

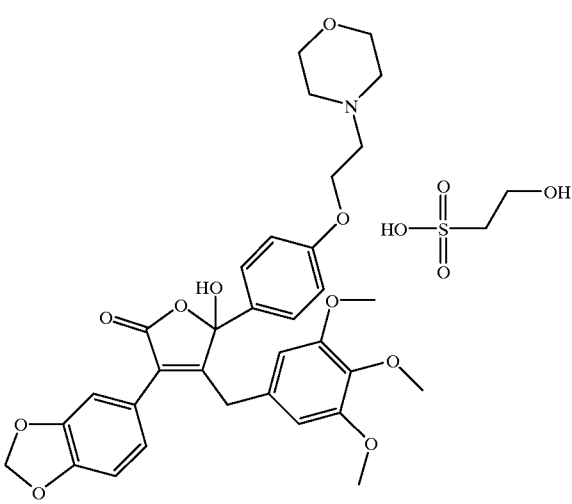

3-Benzo[1,3]dioxol-5-yl-5-hydroxy-5-[4-(2-morpholin-4-yl-ethoxy)-phenyl]-4-(3,4,5-trimethoxy-benzyl)-5H-furan-2-one 2-hydroxyethanesulfonate To methanol (5 mL) was added the butenolide, Example 27, 0.605 g (1.0 mmol) giving solution, followed by addition of 0.42N isethionic acid (2.38 mL). The mixture was evaporated in vacuo to a gum. The gum was dissolved in water (25 mL), filtered at 45 microns, and lyophilized to a solid, 0.717 g, which was identified by $^1$H NMR, MS, and microanalysis.

INTERMEDIATE 15

To 3,4-methylenedioxybenzaldehyde 7.51 g (50 mmol) in absolute ethanol (50 mL) in an Erlenmeyer was added 4-hydroxyacetophenone 6.81 g (50 mmol). The solution was warmed while 12.5% sodium hydroxide (20 mL) added. The mixture was refluxed for 1 hour and allowed to stand overnight at 25° C. The pH was adjusted to 4 with 6N HCl, giving a precipitate. The solid was collected by filtration and washed with water. The solid was dissolved in ethyl acetate, washed with brine, and dried over anhydrous magnesium sulfate. The solution was evaporated in vacuo to a small volume, and the product was precipitated by addition of petroleum ether. The solid was filtered and dried in vacuo giving 9.25 g of a yellow solid, mp 200–204° C., which was identified by $^1$H NMR, MS, and microanalysis.

INTERMEDIATE 16

To the chalcone, Intermediate 15, 8.0 g (29.8 mmol) in dimethylformamide (200 mL) was added cesium carbonate 48.0 g (147 mmol) followed by addition of 3-chloropropyldimethylamine hydrochloride 11.78 g (74.5 mmol). After heating at 90° C. for 2 hours, the mixture was filtered and evaporated to an oil in vacuo. The oil was dissolved in ethyl acetate, and a solid was precipitated by the addition of 1N HCl. The liquid phases were decanted, and the solid was partitioned between ethyl acetate and 2N NaOH, giving solution of the solid. The organic phase was washed with brine, dried over magnesium sulfate, filtered, and evaporated in vacuo to a small volume. Addition of ethyl ether gave a precipitate which was filtered, washed with ethyl ether, and dried in vacuo giving a solid, 6.6 g. The chalcone was identified by $^1$H NMR, MS, and microanalysis.

INTERMEDIATE 17

To the chalcone, Intermediate 16, 6.5 g (18.39 mmol) in 2-ethoxyethanol (50 mL) at 100° C. was added acetic acid 2.66 g (44 mmol) followed by slow addition of potassium cyanide 5.25 g (80.6 mmol) in water (25 mL). The solution was stirred at 120° C. for 20 minutes. The solution was cooled over 1 hour and evaporated in vacuo to a paste. The paste was suspended in a mixture of ethyl acetate and ethyl ether, and filtered. The filtered solid was partitioned between ethyl acetate and water giving solution of the paste. The aqueous phase was extracted exhaustively with ethyl acetate. The organic extract was washed with brine, dried over magnesium sulfate, filtered, and evaporated in vacuo to an oil, 6.11 g. The nitrile was identified by $^1$H NMR, MS, and microanalysis.

INTERMEDIATE 18

To the nitrile, Intermediate 17, 8.11 g (18.4 mmol) was added methanol (60 mL) and dioxane (40 mL). To the mixture was added p-toluenesulfonic acid monohydrate 10 g (53 mmol). The mixture was heated to reflux for 48 hours, and evaporated to an oil. The residue was suspended in ethyl acetate and washed with saturated sodium bicarbonate solution and brine. The organic phase was washed with brine, dried over magnesium sulfate, and evaporated in vacuo to an oil, 5.9 g, identified by $^1$H NMR, MS, and microanalysis.

EXAMPLE 29

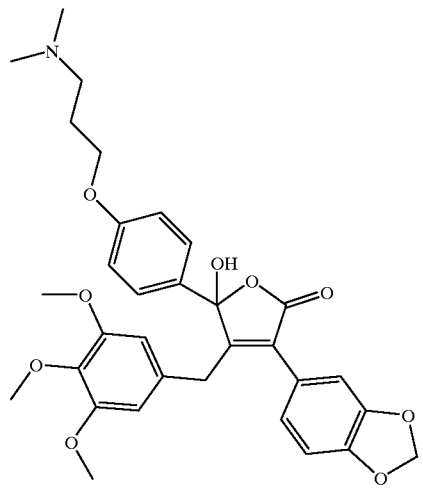

3-Benzo[1,3]dioxol-5-yl-5-[4-(3-dimethylamino-propoxy)-phenyl]-5-hydroxy-4-(3,4,5-trimethoxy-benzyl)-5H-furan-2-one To methanol (50 mL) was added sodium metal 0.337 9 (36.5 mmol) and stirred to dissolve. To this was added the ester, Intermediate 18, 5.8 9 (14.0 mmol) then 3,4,5-trimethoxybenzaldehyde 3.42 g (17.4 mmol). The mixture was heated to reflux for 18 hours. The solution was then treated with acetic acid (5 mL) and refluxed an additional 5 hours. The solvents were removed by evaporation, and the residue was partitioned between ether (100 mL) and 1N sodium hydroxide (100 mL). The aqueous phase was separated and acidified to pH 8 with 6N HCl. This solution was extracted with 100 mL ethyl acetate. The organic phase was separated, washed with brine, dried over magnesium sulfate, and evaporated in vacuo). This gave the butenolide 1.62 g

45

(20%) as a solid. The butenolide was identified by $^1$H NMR, MS, [M+H]$^+$=578 Da., and microanalysis.

EXAMPLE 30

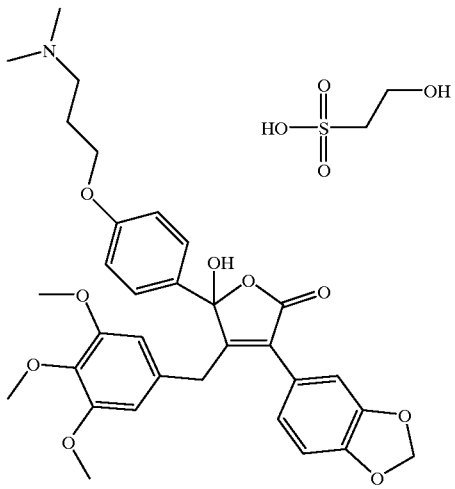

3-Benzo[1,3]dioxol-5-yl-5-[4-(3-dimethylamino-propoxy)-phenyl]-5-hydroxy-4-(3,4,5-trimethoxy-benzyl)-5H-furan-2-one 2-hydroxyethanesulfonate To methanol (5 mL) was added the butenolide, Example 29, 0.50 g (0.866 mmol) giving solution, followed by addition of 0.42N isethionic acid (2.06 mL). The mixture was evaporated in vacuo to a gum. The gum was dissolved in water (25 mL), filtered at 45 microns, and lyophilized to a solid, 0.56 g, which was identified by $^1$H NMR, MS, and microanalysis.

INTERMEDIATE 19

To methanol (80 mL) was added sodium metal 0.48 9 (21 mmol) and stirred to dissolve. To this was added the ester, 2-Benzo[1,3]dioxol-5-yl-1-(4-methoxyphenyl)-4-oxo-butyric acid methyl ester, 6.84 g (19.9 mmol) then m-nitrobenzaldehyde 3.48 g (23 mmol). The mixture was heated to reflux for 16 hours. The solution was then treated with acetic acid (9 mL) and refluxed an additional 15 hours. The solvents were removed by evaporation, and the resulting solid was suspended in ethyl ether and water, filtered, washed with ether, and dried in vacuo to a solid, 7.73 g (84%). The butenolide was identified by $^1$H NMR, MS, [M+H]$^+$=462 Da., and microanalysis.

INTERMEDIATE 20

To tetrahydrofuran (75 mL) was added Raney Nickel paste 0.48 g (Davison Chemical, Lot 5125). To this was added the butenolide, Intermediate 19, 0.412 g (0.893 mmol). The mixture was purged with H$_2$ for 2 hours. The solution was then filtered, evaporated in vacuo, and the residue resuspended in ethyl ether. Addition of hexane gave a white solid which was filtered and dried in vacuo, 0.322 g (84%). The butenolide was identified by IH NMR, MS, [M+H]$^+$=432 Da., and microanalysis.

46

EXAMPLE 31

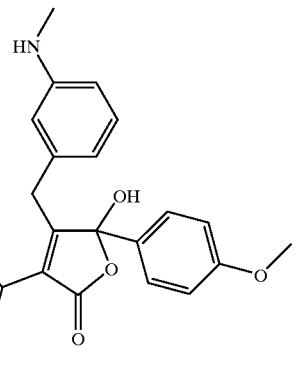

3-Benzo[1,3]dioxol-5-yl-5-hydroxy-5-(4-methoxy-phenyl)-4-(3-methylamino-benzyl)-5H-furan-2-one To a mixture of 95% ethanol (45 mL) and tetrahydrofuran (30 mL) was added Raney Nickel paste 0.2 g (Davison Chemical) and 37% formaldehyde solution 0.1 g (1.11 mmol). To this was added the butenolide, Intermediate 20, 0.48 g (1.11 mmol). The mixture was pressurized with H$_2$ gas at 30 psi for 18 hours. The solution was then filtered, evaporated in vacuo, and the residue purified by chromatography on silica gel (50 g), eluted with a gradient of 10% to 30% ethyl acetate in hexane. Addition of ethyl ether followed by drying in vacuo gave a white solid, 0.23 g (46%). The butenolide was identified by $^1$H NMR, MS, [M+H]$^+$=445 Da., and microanalysis.

INTERMEDIATE 21

Dimethylamine gas 32 g (718 mmol) was condensed into benzene (300 mL) at 0° C., and 3-bromobenzyl bromide 54.99 (219;6 mmol) in benzene (100 mL) was then added. After stirring 48 hours at 25° C., the mixture was washed with 4N sodium hydroxide solution and extracted with 4N HCl. The extract was adjusted to pH 14 with 4N sodium hydroxide solution and extracted with ethyl ether. The ether phase was washed with brine, dried over magnesium sulfate, and filtered. The filtrate was evaporated in vacuo to an oil, 45.9 g. The oil was distilled to a clear oil, 36.2 g, bp 78–84° C. at 0.75 mm Hg, which was identified by $^1$H NMR, MS, and microanalysis.

INTERMEDIATE 22

To dry, tetrahydrofuran (100 mL) was added magnesium turnings 4.09 g (168 mmol) followed by the gradual addition of a solution of Intermediate 21,36 g (168 mmol), in dry ethyl ether (75 mL). After 1 hour the addition was complete, and the temperature was held at reflux for 2 hours. The mixture was cooled to −50° C., and a solution of dimethylformamide 12.28 g (168 mmol) in dry ethyl ether (75 mL) was added. The mixture was stirred at 25° C. for 18 hours, then poured into 250 mL cold 6N HCl. The phases were separated, and the aqueous phase was adjusted to pH 14 with 2N sodium hydroxide solution. The mixture was extracted into ethyl ether and washed with brine, dried over magnesium sulfate, and filtered. Evaporation under reduced pressure gave an oil which was purified by chromatography on 1300 g silica gel eluted with a gradient of 50% hexane and 50% ethyl acetate to 20% methanol and 80% ethyl acetate. The product was distilled giving an oil, (18 g), bp 80–85° C. at 1.5 mm Hg, which was identified by $^1$H NMR, MS, and microanalysis.

EXAMPLE 32

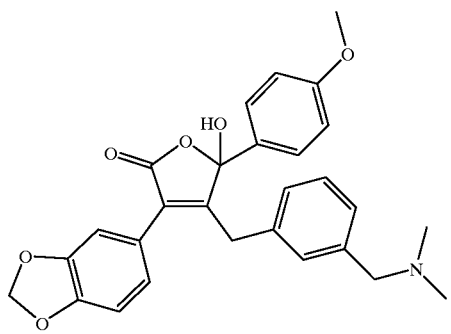

3-Benzo[1,3]dioxol-5-yl-4-(3-dimethylaminoethyl-benzyl)-5-hydroxy-5-(4-methoxy-phenyl)-5H-furan-2-one To methanol (50 mL) was added sodium metal 0.271 g (11.8 mmol) and stirred to dissolve. To this was added the ester, 2-Benzo[1,3]dioxol-5-yl-1-(4-methoxyphenyl)-4-oxo-butyric acid methyl ester, 3.85 g (11.25 mmol) then Intermediate 22, 2.11 g (12.93 mmol). The mixture was heated to reflux for 16 hours. The solution was then treated with acetic acid (5 mL) and refluxed an additional 16 hours. The solvents were removed by evaporation, and the residue was partitioned between ether (100 mL) and water (100 mL). The aqueous phase was adjusted to pH 13 with 2N sodium hydroxide, and was washed with ethyl ether. The aqueous phase was then acidified to pH 4 with 2N HCl giving a solid precipitate. The solid was filtered, washed with ethyl ether and water, and partitioned between ethyl acetate and water at pH 10, giving solution of the solid. The organic phase was washed with brine, dried over magnesium sulfate, and filtered. Evaporation of the solution in vacuo gave a white foam, 2.75 g (52w). The butenolide was identified by $^1$H NMR, MS, [M+H]$^+$=474 Da., and microanalysis.

EXAMPLE 33

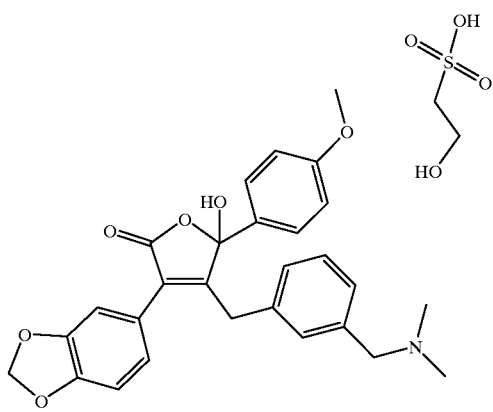

3-Benzo[1,3]dioxol-5-yl-4-(3-dimethylaminomethyl-benzyl)-5-hydroxy-5-(4-methoxy-phenyl)-5H-furan-2-one 2-hydroxyethanesulfonate To methanol (5 mL) was added the butenolide, Example 32, 0.473 g (1.0 mmol) giving solution, followed by addition of 0.42N isethionic acid (2.33 mL). The mixture was evaporated in vacuo to a gum. The gum was dissolved in water (25 mL), filtered at 45 microns, and lyophilized to a solid, 0.58 9, which was identified by $^1$H NMR, MS, and microanalysis.

EXAMPLE 34

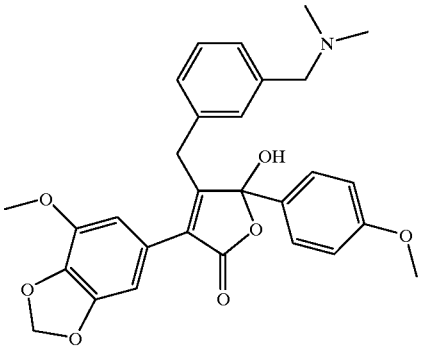

4-(3-Dimethylaminomethyl-benzyl)-5-hydroxy-3-(7-methoxy-benzo[1,3]dioxol-5-yl)-5-(4-methoxy-phenyl)-5H-furan-2-one To methanol (50 mL) was added sodium metal 0.271 g (11.8 mmol) and stirred to dissolve. To this was added the ester, 2-[7-methoxy-benzo[1,3]dioxol]-5-yl-1-(4-methoxyphenyl)-4-oxo-butyric acid methyl ester, 4.19 g (11.25 mmol) then Intermediate 22, 2.11 g (12.93 mmol). The mixture was heated to reflux for 16 hours. The solution was then treated with acetic acid (5 mL) and refluxed an additional 16 hours. The solvents were removed by evaporation, and the residue was partitioned between ether (100 mL) and water (100 mL). The aqueous phase was adjusted to pH 13 with 4N sodium hydroxide, giving an oily precipitate. Decant the oil and partition it between ethyl acetate and water. Adjust pH to 9 with 6N HCl, separate phases, and wash the organic phase with brine. The organic phase was dried over magnesium sulfate, filtered, and evaporated in vacuo to a small volume. Trituration with ethyl ether gave a white solid which was collected and dried in vacuo, 3.2 g. The butenolide was identified by $^1$H NMR, MS, [M+H]$^+$=504 Da., and microanalysis.

EXAMPLE 35

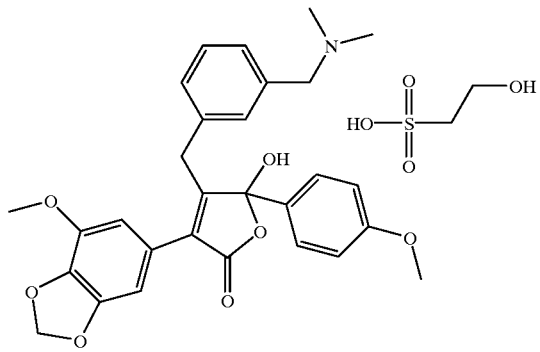

4-(3-Dimethylaminomethyl-benzyl)-5-hydroxy-3-(7-methoxy-benzo[1,3]dioxol-5-yl)-5-(4-methoxy-phenyl)-5H-furan-2-one 2-hydroxyethanesulfonate To water (20 mL) was added the butenolide, Example 34, 0.568 g (1.0 mmol) followed by addition of 0.42N isethionic acid (2.82 mL) giving solution. The mixture was evaporated in vacuo to a gum. The gum was dissolved in water (25 mL), filtered at 45 microns, and lyophilized to a solid, 0.654 g, which was identified by $^1$H NMR, MS, and microanalysis.

EXAMPLE 36

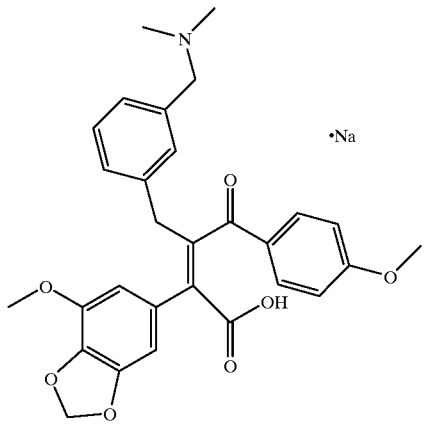

3-(3-Dimethylaminomethyl-benzyl)-2-(7-methoxy-benzo[1,3]dioxol-5-yl)-4-(4-methoxy-phenyl)-4-oxo-but-2-enoic-acid sodium salt The butenolide, Example 34, 0.828 g (1.645 mmol) was added to 1.001N sodium hydroxide (1.64 mL) giving solution, followed by dilution with water to (25 mL). The solution was filtered at 45 microns, and lyophilized to a solid, 0.793 g, which was identified by $^1$H NMR, MS, and microanalysis.

EXAMPLE 37

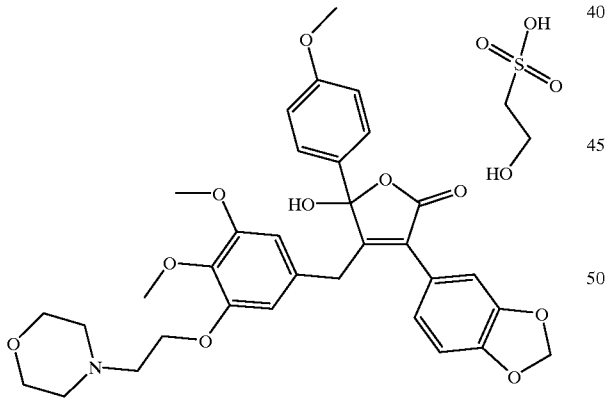

3-Benzo[1,3]dioxol-5-yl-4-[3,4-dimethoxy-5-(2-morpholin-4-yl-ethoxy)-benzyl]-5-hydroxy-(4-methoxy-phenyl)-5-furan-2-one 2-hydroxyethanesulfonate In a manner similar to Example 4, Example 2 (230 mg, 0.380 mmol) was converted to the salt with isethionic acid (900 µL of 0.42 (aq.), 0.380 mmol). This gave 260 mg (94%) which was identified by 1H NMR, IR, MS, [M+H]$^+$=606 Da., and microanalysis.

EXAMPLE 38

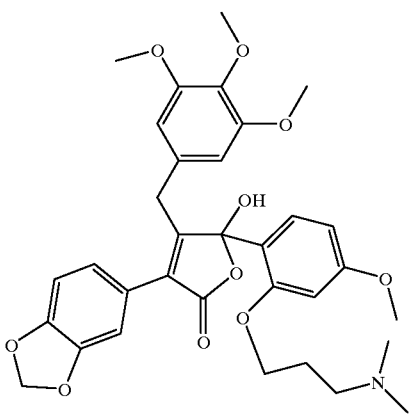

3Benzo[1,3]dioxol-5-yl-5-[2-(3-dimethylamino-propoxy)-4-methoxy-phenyl]-5-hydroxy-4-(3,4,5-trimethoxy-benzyl)-5H-furan-2-one To methanol (50 mL) was added sodium metal 0.337 g (14.7 mmol) and stirred to dissolve. To this was added the ester, Intermediate 10, 6.21 g (14.0 mmol) then 3,4,5-trimethoxybenzaldehyde 3.42 g (17.4 mmol). The mixture was heated to reflux for 16 hours. The solution was then treated with acetic acid (8 mL) and refluxed an additional 16 hours. The solvents were removed by evaporation, and the residue was partitioned between ether (100 mL) and water (100 mL) giving a suspension. The aqueous phase was adjusted to pH 14 with 6N sodium hydroxide, giving solution of the solids. The ether phase was decanted, and the aqueous phase was adjusted to pH 9 with 6N HCl, giving a precipitate. The solid was filtered and washed with water and ethyl ether. The solid was dried in vacuo, 6.17 g. The solid was further purified by chromatography on silica gel, 250 g, and eluted with a gradient of 5% to 10% methanol in chloroform. A solid was recovered from an ethyl acetate/ethyl ether, 4.22 g (49%). The butenolide was identified by $^1$H NMR, MS, [M+H]$^+$=608 Da., and microanalysis.

What is claimed is:

1. A compound of formula

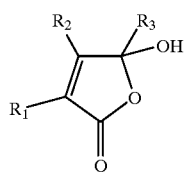

I or a tautomeric open chain keto-acid form thereof or a pharmaceutically acceptable salt thereof wherein $R_1$ is cycloalkyl of from 3 to 12 carbon atoms substituted or unsubstituted, phenyl substituted with from 1 to 5 substituents, naphthyl unsubstituted or substituted with from 1 to 5 substituents, or heteroaryl unsubstituted or substituted with from 1 to 5 substituents;

$R_2$ is straight or branched alkyl of from 1 to 12 carbon atoms substituted or unsubstituted, cycloalkyl of from 3 to 12 carbon atoms substituted or unsubstituted, aryl unsubstituted or substituted with from 1 to 5 substituents, or heteroaryl unsubstituted or substituted with from 1 to 3 substituents;

R₃ is straight or branched alkyl of from 1 to 12 carbon atoms substituted or unsubstituted, cycloalkyl of from 3 to 12 carbon atoms substituted or unsubstituted, aryl which is unsubstituted or substituted with from 1 to 5 substituents, or heteroaryl unsubstituted or substituted with from 1 to 3 substituents; and at least one of R₁ or R₂ or R₃ is independently substituted by a total of from 1 to 4 substituents which enhance aqueous solubility, said substituents independently selected from the group consisting of:

sulfonic acid or SO₃H groups and amino groups selected from the group consisting of morpholinyl, pyrrolidinyl, and piperazinyl, with the proviso that when R₂ is alkyl and is substituted, the substituent is not oxygen at the α-position to the furanone ring.

2. A compound according to claim 1 wherein

R₁ is phenyl substituted with from 1 to 5 substituents,

R₂ is straight or branched alkyl of from 1 to 9 carbon atoms substituted with from 1 to 7 substituents, R₃ is aryl substituted or unsubstituted; and at least one of Groups R₁ or R₂ or R₃ is independently substituted by a total of from 1 to 4 substituents which enhance aqueous solubility, said substituents are independently selected from the group consisting of sulfonic acid or SO₃H groups and amino groups selected from the group consisting of morpholinyl, pyrrolidinyl, and piperazinyl, with the proviso when R₂ is alkyl and is substituted, the substituent is not oxygen at the α-position to the furanone ring.

3. A compound according to claim 1 wherein

R₁ is phenyl substituted with from 1 to 5 substituents;

R₂ is straight or branched alkyl of from 1 to 7 carbons substituted with from 1 to 7 substituents;

R₃ is aryl substituted or unsubstituted; and at least one of the substituents on R₁ and/or R₂ and/or R₃ have a substituent selected from:

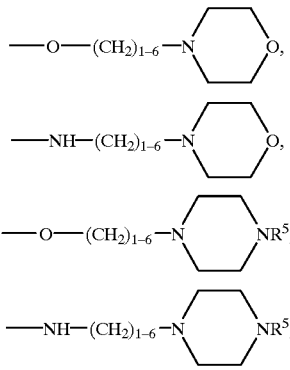

wherein R⁵ is hydrogen or lower alkyl,

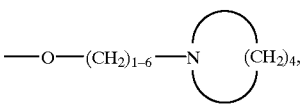

-continued

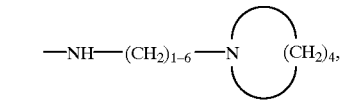

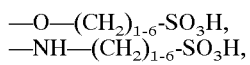

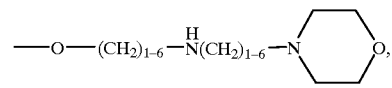

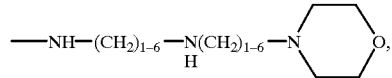

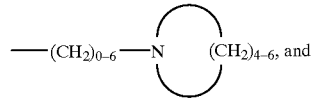

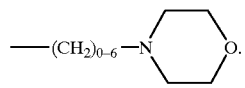

4. A compound according to claim 1 wherein

R₁ is piperonyl,
   3,5-dimethoxyphenyl, or
   3-methoxy-4,5-methylenedioxyphenyl;

R₂ is 4-(3-dimethylaminopropoxy)benzyl,
   3-(3-dimethylaminopropoxy)benzyl,
   5-(3-dimethylaminopropoxy)-3,4-dimethoxybenzyl,
   5-(2-morpholin-4-yl-ethoxy)-3,4-dimethoxybenzyl,
   5-(3-morpholin-4-yl-propoxy)-3,4-dimethoxybenzyl,
   5-(3-(4-methyl-piperazin-1-yl)propoxy)-3,4-dimethoxybenzyl,
   5-(2-(4-methyl-piperazin-1-yl)ethoxy)-3,4-dimethoxybenzyl,
   4-(2-(4-methyl-piperazin-1-yl)ethoxy)benzyl,
   3-(2-(4-methyl-piperazin-1-yl)ethoxy)benzyl,
   4-(3-(4-methyl-piperazin-1-yl)propoxy)benzyl,
   3-(3-(4-methyl-piperazin-1-yl)propoxy)benzyl,
   4-(2-morpholin-4-yl-ethoxy)benzyl,
   3-(2-morpholin-4-yl-ethoxy)benzyl,
   4-(2-pyrrolidinyl-ethoxy)benzyl,
   3-(2-pyrrolidinyl-ethoxy)benzyl,
   4-(3-pyrrolidinyl-propoxy)benzyl,
   3-(3-pyrrolidinyl-propoxy)benzyl,
   5-(3-pyrrolidinyl-propoxy)-3,4-dimethoxybenzyl,
   5-(2-pyrrolidinyl-ethoxy)-3,4-dimethoxybenzyl,
   3,4,5-trimethoxybenzyl, benzyl;

R₃ is 3,4-dimethoxyphenyl,
   3-methyl-4-methoxyphenyl,
   2,4-dimethoxyphenyl,
   4-methoxyphenyl,
   4-(3-dimethylaminopropoxy)phenyl, or
   4-(2-morpholin-4-ylethoxy)phenyl;

R4 is hydroxy; and at least one R₁ and/or R₂ and/or R₃ is independently substituted by a total of from 1 to 4 substituents which enhance aqueous solubility, said substituents are independently selected from the group consisting of sulfonic acid or SO₃H groups and amino groups selected from the group consisting of morpholinyl, pyrrolidinyl, and piperazinyl, with the proviso when R₂ is alkyl and is substituted, the substituent is not oxygen at the α-position to the furanone ring.

5. A compound according to claim 1 and selected from

2-{5-[4-Benzo[1,3]dioxol-5-yl-2-hydroxy-2-(4-methoxy-phenyl)-5-oxo-2,5-dihydr-furan-3-ylmethyl]-2,3-dimethoxy-phenoxy}-N-(2-morpholin-4-yl-ethyl)-acetamide, 3-Benzo[1,3]dioxol-5-yl-5-hydroxy-5-[4-(2-morpholin-4-yl-ethoxy)-phenyl]-4-(3,4,5-trimethoxy-benzyl)-5H-furan-2-one, 3-Benzo[1,3]dioxol-5-yl-4-[3,4-dimethoxy-5-(2-morpholin-4-yl-ethoxy)-benzyl]-5-hydroxy-5-(4-methoxy-phenyl)-5H-furan-2-one, 3-Benzo[1,3]dioxol-5-yl-5-hydroxy-5-(4-methoxy-phenyl)-4-[3-(2-morpholin-4yl-ethoxy)-benzyl]-5H-furan-2-one, 3-Benzo[1,3]dioxol-5-yl-5-hydroxy-4-[3-methoxy-4,5-bis-(2-morpholin-4-yl-ethoxy)-benzyl]-5-(4-methoxy-phenyl)-5H-furan-2-one, 3-Benzo[1,3]dioxol-5-yl-4-[3,4-dimethoxy-5-(3-morpholin-4-yl-propoxy)-benzyl]-5-hydroxy-5-(4-methoxy-phenyl)-5H-furan-2-one, 3-Benzo[1,3]dioxol-5-yl-4-{3,4-dimethyoxy-5-[3-(4-methyl-piperazin-1-yl)-propoxy]-benzyl}-5-hydroxy-5-(4-methoxy-phenyl)-5H-furan-2-one, 3-{5-[4-Benzo[1,3]dioxol-5-yl-2-hydroxy-2-(4-methoxy-phenyl)-5-oxo-2,5-dihydro-furan-3-ylmethyl]-2,3-dimethoxy-phenoxy}-propane-1-sulfonic acid, 3-Benzo[1,3]dioxol-5-yl-5-hydroxy-5-(4-methoxy-phenyl)-4-[3-(3-morpholin-4-yl-propoxy)-benzyl]-5H-furan-2-one, 3-Benzo[1,3]dioxol-5-yl-5-hydroxy-5-(4-methoxy-phenyl)-4-{3-[3-(4-methyl-piperazin-1-yl)-propoxy]-benzyl}-5H-furan-2-one, and 4-{3,4-Dimethoxy-5-[3-(4-methyl-piperazin-1-yl)-propoxy]-benzyl}-3-(3,5-dimethoxy-phenyl)-5-hydroxy-5-(4-methoxy-phenyl)-5H-furan-2-one.

6. A pharmaceutical composition comprising a therapeutically effective amount of a compound according to claim 1 in admixture with a pharmaceutically acceptable excipient, diluent, and/or carrier.

7. A method of inhibiting elevated levels of endothelin comprising administering to a host suffering therefore a therapeutically effective amount of a composition according to claim 1 in unit dosing form.

8. A method of treating vascular diseases selected from therosclerosis, restenosis, and Raynaud's phenomenon comprising administering to a host suffering therefrom a therapeutically effective amount of a compound according to claim 1 in unit dosage form.

9. A method of treating mild or severe congestive heart failure comprising administering to a host suffering therefrom a therapeutically effective amount of a compound according to claim 1 in unit dosage form.

10. A method of treating cerebral ischemia, cerebral infarction, or embolic stroke, comprising administering to a host suffering therefrom a therapeutically effective amount of a compound according to claim 1 in unit dosage form.

11. A method of treating cerebral vasospasm, subarachnoid hemorrhage or hemorrhagic stroke comprising administering to a host suffering therefrom a therapeutically effective amount of a compound according to claim 1 in unit dosage form.

12. A method of treating diabetes comprising administering to a host suffering therefrom a therapeutically effective amount of a compound according to claim 1 in unit dosage form.

13. A method of treating gastric ulceration and mucosal damage, ischemic bowel disease, or Chrohn's disease comprising administering to a host suffering therefrom a therapeutically effective amount of a compound according to claim 1 in unit dosage form.

14. A method of treating essential and malignant hypertension comprising administering to a host suffering therefrom a therapeutically effective amount of a compound according to claim 1 in unit dosage form.

15. A method of treating pulmonary hypertension or pulmonary hypertension after bypass surgery comprising administering to a host suffering therefrom a therapeutically effective amount of a compound according to claim 1 in unit dosage form.

16. A method of treating cancer selected from meningiomas, malignant hemangioendothelioma and prostate cancer, comprising administering to a host suffering therefrom a therapeutically effective amount of a compound according to claim 1 in unit dosage form.

17. A method of treating myocardial infarction or ischemia comprising administering to a host suffering therefrom a therapeutically effective amount of a compound according to claim 1 in unit dosage form.

18. A method of treating acute or chronic renal failure, renal ischemia, or radiocontrast-induced nephrotoxicity comprising administering to a host suffering therefrom a therapeutically effective amount of a compound according to claim 1 in unit dosage form.

19. A method of treating endotoxic, septic or hemorrhagic shock comprising administering to a host suffering therefrom a therapeutically effective amount of a compound according to claim 1 in unit dosage form.

20. A method of treating angina comprising administering to a host suffering therefrom a therapeutically effective amount of a compound according to claim 1 in unit dosage form.

21. A method of treating preeclampsia comprising administering to a host suffering therefrom a therapeutically effective amount of a compound according to claim 1 in unit dosage form.

22. A method of treating asthma comprising administering to a host suffering therefrom a therapeutically effective amount of a compound according to claim 1 in unit dosage form.

23. A method of treating arrhythmias comprising administering to a host suffering therefrom a therapeutically effective amount of a compound according to claim 1 in unit dosage form.

24. A method of treating benign prostatic hyperplasia comprising administering to a host suffering therefrom a therapeutically effective amount of a compound according to claim 1 in unit dosage form.

25. A method of treating glaucoma comprising administering to a host suffering therefrom a therapeutically effective amount of a compound according to claim 1 in unit dosage form.

26. A method of treating male penile erectile dysfunction comprising administering to a host suffering therefrom a therapeutically effective amount of a compound according to claim 1 in unit dosage form.

27. A method of treating cryptogenic fibrosing alveolitis comprising administering to a host suffering therefrom a therapeutically effective amount of a compound according to claim 1 in unit dosage form.

28. A process for the preparation of nonpetide endothelin antagonists with increased water solubility of Formula I above comprising:

1) condensing an aldehyde of Formula

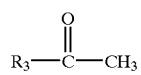

with acetophenone-type compound, R$_1$—CHO, in basic solution to product a chalcone derivative,

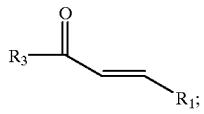

2) treating the product of Step 1) above with HCN in a solvent to produce a nitrile,

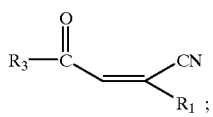

3) hydrolyzing the nitrile of Step 2) above with an acidic solution to product the ester,

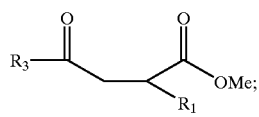

4) condensing the ester from Step 3) above with an aldehyde, R-CHO, in solvent using a base and cyclizing it with acid to produce a compound of Formula I as in claim 1.

29. A process for the preparation of nonpeptide endothelin antagonists with increased water solubility of Formula I above comprising:

1) treating a butenolide containing a leaving group selected from halogen, mesylate, tosylate, or triflate at R$_1$, R$_2$, or R$_3$ (R$_2$ is shown),

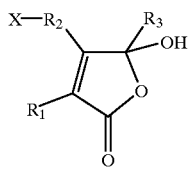

with a primary amine, secondary amine, or sodium sulfite to produce a compound,

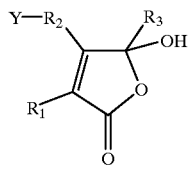

where Y is a morpholinyl group, a pyrrolidinyl group, a piperazinyl group, or sulfonic acid (sodium salt).

* * * * *